United States Patent
Sgroi

(10) Patent No.: US 11,517,317 B2
(45) Date of Patent: Dec. 6, 2022

(54) TROCAR RELEASE ASSEMBLIES FOR A SURGICAL STAPLER

(71) Applicant: Covidien LP, Mansfield, MA (US)

(72) Inventor: Anthony Sgroi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 79 days.

(21) Appl. No.: 17/142,695

(22) Filed: Jan. 6, 2021

(65) Prior Publication Data

US 2021/0204952 A1 Jul. 8, 2021

Related U.S. Application Data

(60) Provisional application No. 62/957,387, filed on Jan. 6, 2020.

(51) Int. Cl.
*A61B 17/064* (2006.01)
*A61B 17/115* (2006.01)
*A61B 17/34* (2006.01)

(52) U.S. Cl.
CPC .......... *A61B 17/1155* (2013.01); *A61B 17/34* (2013.01)

(58) Field of Classification Search
CPC .. A61B 2017/0046; A61B 2017/00473; A61B 2017/00477
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |

(Continued)

FOREIGN PATENT DOCUMENTS

| | | |
|---|---|---|
| CA | 908529 A | 8/1972 |
| CA | 2805365 A1 | 8/2013 |

(Continued)

*Primary Examiner* — Eyamindae C Jallow
(74) *Attorney, Agent, or Firm* — Carter, DeLuca & Farrell LLP

(57) ABSTRACT

A trocar release assembly includes a housing, a release button, first and second springs, and a pin. The housing has top and bottom faces, side faces, and end faces. The end faces include opposed openings that define a passage between. The passage is configured to receive a sleeve of a trocar assembly. The release button is movably coupled to the housing and is movable between a compressed position and an expanded position. The first spring is positioned between the housing and the release button to bias the release button towards the expanded position. The pin slides within a chamber of the housing and is slidable between a retracted position and an extended position. The second spring is operably coupled with the pin to bias the pin towards an extended position.

21 Claims, 23 Drawing Sheets

(56) References Cited

U.S. PATENT DOCUMENTS

| | | |
|---|---|---|
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |

(56) References Cited

U.S. PATENT DOCUMENTS

| | | |
|---|---|---|
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |

(56) References Cited

U.S. PATENT DOCUMENTS

| | | |
|---|---|---|
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,806,973 B2 | 8/2014 | Ross et al. |
| 10,973,544 B2 * | 4/2021 | Williams ............ A61B 17/072 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |

(56) References Cited

U.S. PATENT DOCUMENTS

| | | |
|---|---|---|
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0086879 A1* | 3/2017 | Williams ............... A61B 17/115 |
| 2017/0196566 A1* | 7/2017 | Sgroi ...................... A61B 17/34 |
| 2017/0224345 A1 | 8/2017 | Cabrera et al. |
| 2017/0333077 A1* | 11/2017 | Williams ............... A61B 17/34 |
| 2018/0280024 A1* | 10/2018 | Williams ........... A61B 17/1155 |
| 2020/0222051 A1* | 7/2020 | Eisinger ............ A61B 17/1155 |
| 2021/0000472 A1* | 1/2021 | Sgroi, Jr. ............. A61B 17/072 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3146905 A1 | 3/2017 |
| EP | 3192462 A1 | 7/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

\* cited by examiner

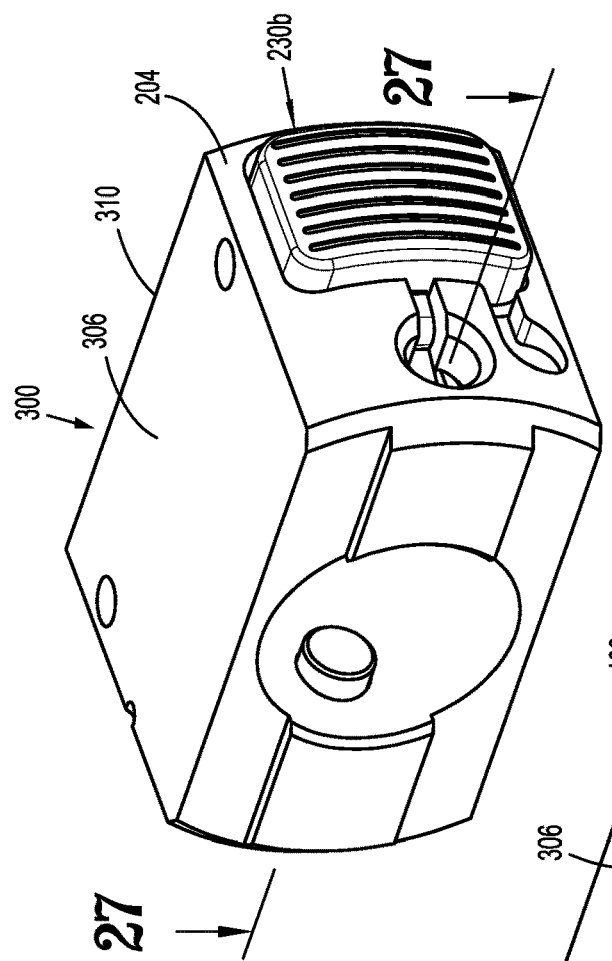
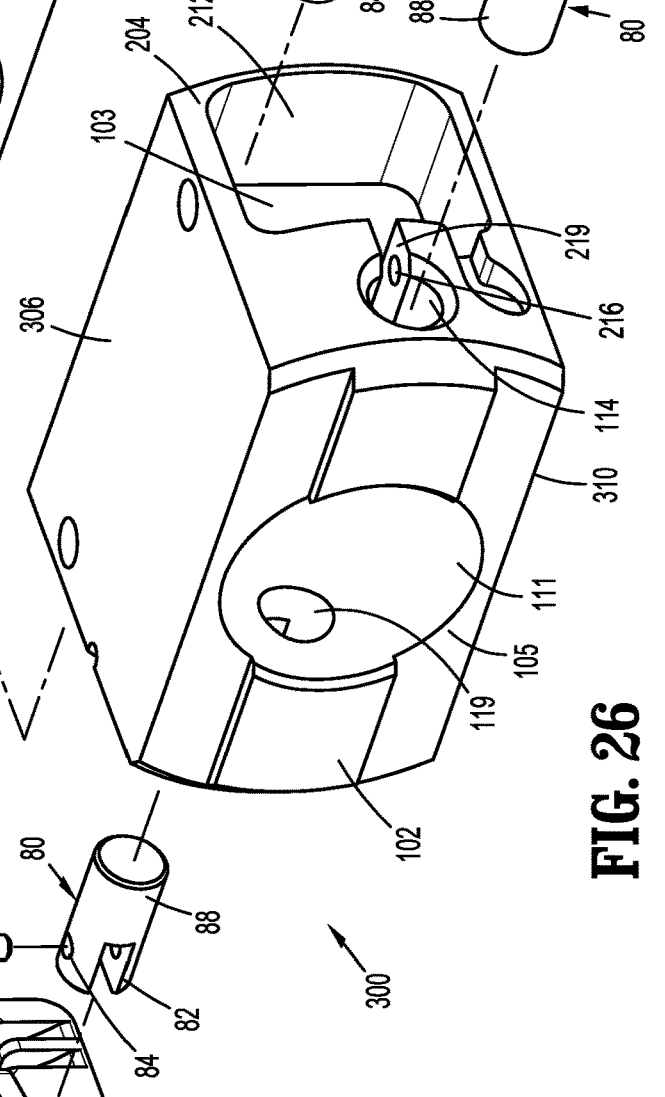
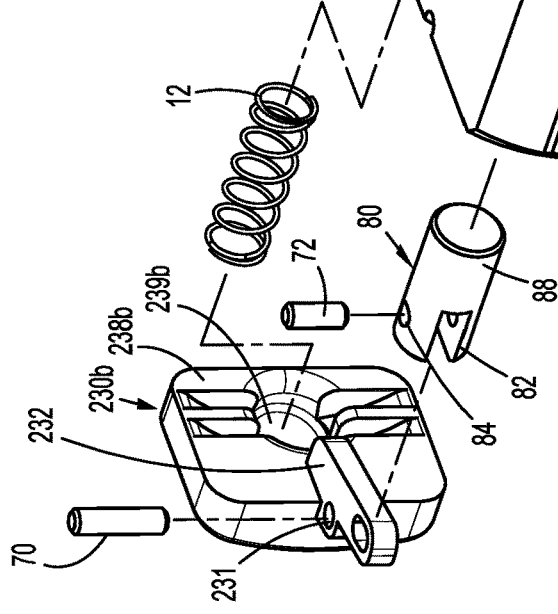
FIG. 25
FIG. 26

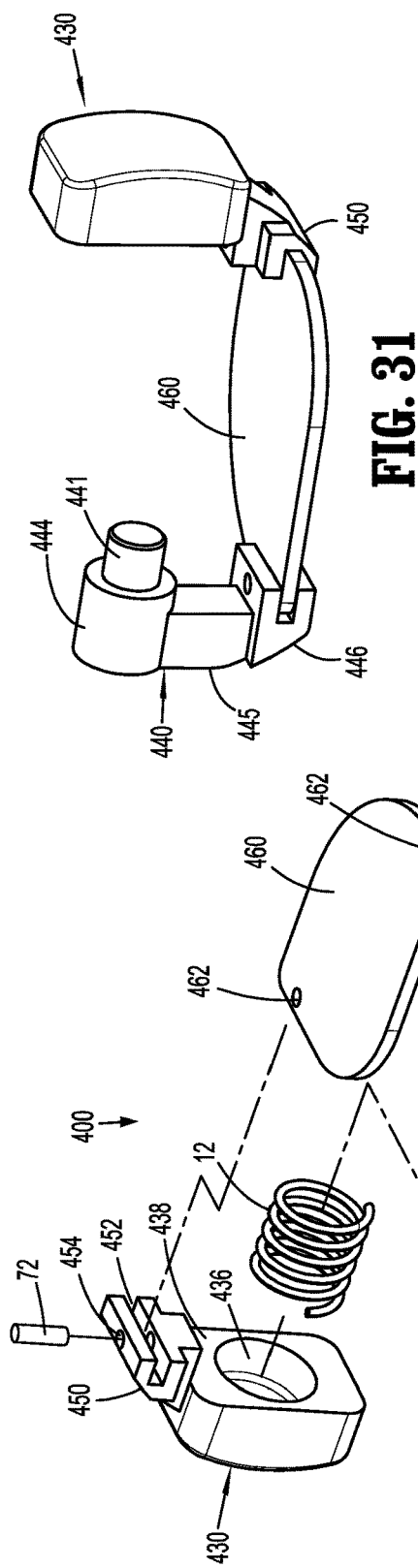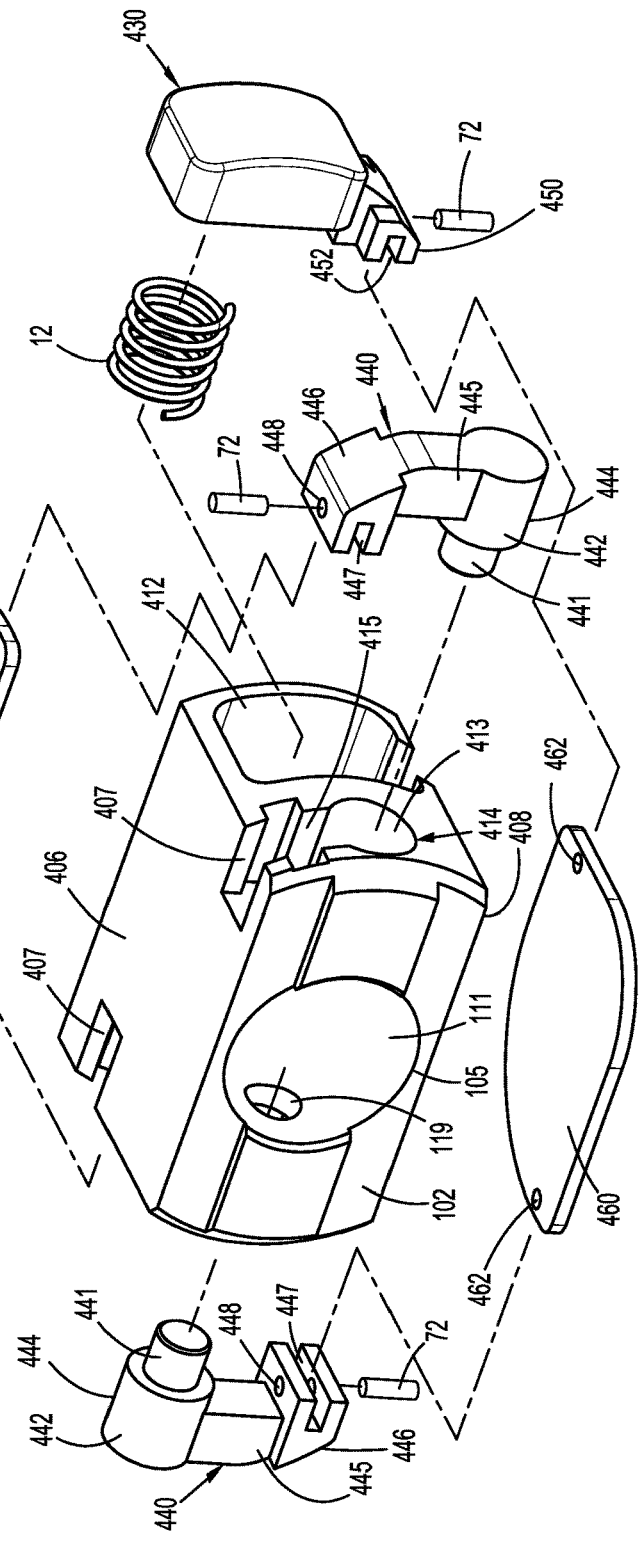

TROCAR RELEASE ASSEMBLIES FOR A SURGICAL STAPLER

CROSS-REFERENCE TO RELATED APPLICATIONS

This application claims the benefit of and priority to U.S. Provisional Patent Application Ser. No. 62/957,387 filed Jan. 6, 2020, the entire disclosure of which is incorporated by reference herein.

BACKGROUND

Technical Field

The present disclosure relates generally to assemblies for retaining a trocar assembly of a surgical stapler. More particularly, the present disclosure relates to assemblies for releasably retaining a trocar assembly partially within an elongated body portion of a surgical stapler.

Background of Related Art

Anastomosis is the surgical joining of separate hollow organ sections. Typically, an anastomosis procedure follows surgery in which a diseased or defective section of hollow tissue is removed, and the end sections are stapled via a surgical stapler. Depending on the desired anastomosis procedure, the end sections may be joined by circular or side-to-side organ reconstruction methods, for instance.

In a circular anastomosis procedure, the two ends of the organ sections are joined by means of a surgical stapler which drives a circular array of staples through the end section of each organ section and simultaneously cores any tissue interior of the driven circular array of staples to free the tubular passage. Typically, these surgical staplers include an elongated body portion having a handle portion at a proximal end to actuate the surgical stapler and a staple holding component disposed at a distal end. An anvil assembly including an anvil retention rod with an attached anvil head is mounted to a trocar assembly at the distal end of the surgical stapler adjacent the staple-holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is advanced to core tissue within the hollow organ to free a tubular passage within the organ.

Besides anastomosis of hollow organs, surgical staplers for performing circular anastomosis have been used to treat internal hemorrhoids in the rectum. Typically, during use of a surgical stapler for hemorrhoid treatment, the anvil head and the staple holding-component of the surgical stapler are inserted through the anus and into the rectum with the anvil head and the staple-holding component in an open or unapproximated position. Thereafter, a purse string suture is used to pull the internal hemorrhoidal tissue towards the anvil rod. Next, the anvil head and staple-holding component are approximated to clamp the hemorrhoidal tissue between the anvil head and the staple holding component. During the approximation of the anvil head and the staple-holding component, the trocar assembly engages the anvil retention rod. The surgical stapler is fired to remove the hemorrhoidal tissue and staple the cut tissue.

It may be desirable to select a particular trocar assembly depending on the type of surgical procedure being performed. Further, it may be helpful to remove the trocar assembly after use to facilitate the sanitization thereof, if reusing the trocar assembly is desired, for instance.

SUMMARY

In an embodiment of the present disclosure, a trocar release assembly for a surgical stapler includes a housing having opposed openings defining a passage therethrough that is configured to receive a sleeve of a trocar assembly therein, a release button movably coupled to the housing and movable between an extended position and a compressed position, a first spring disposed between the housing and the release button, the first spring biasing the release button towards the extended position, a pin slidably disposed in a chamber of the housing, the pin slidable between an extended position and a retracted position, and a second spring operatively coupled with the pin, the second spring biasing the pin towards the extended position.

Moving the release button towards the compressed position may slide the pin towards the extended position. The compressed position of the release button and the retracted position of the pin may define an unlocked configuration of the trocar release assembly.

A distal portion of the pin may engageable with a slot in an outer surface of a sleeve of a trocar assembly to maintain a fixed axial relationship between the trocar release assembly and a trocar assembly.

In embodiments, the trocar release assembly may include a sphere disposed between a prong of the release button and a ramp of the pin. The sphere may operatively couple the release button and the pin. Movement of the release button towards the compressed position may propel the sphere along the ramp such that the pin slides towards the retracted position.

A sleeve of a trocar assembly may be insertable into the passage of the housing with the trocar release assembly in the unlocked configuration.

In embodiments, the trocar release assembly may include a plunger having a sloped portion and a third spring. The plunger and the third spring may be disposed between a prong of the release button and the pin. The third spring may bias the plunger towards the prong of the release button. Movement of the release button towards the compressed position may push the sloped portion of the plunger into engagement with an arm of the pin such that the pin slides towards the retracted position.

According to an embodiment of the present disclosure, a trocar release assembly for a surgical stapler includes a housing having opposed openings defining a passage therethrough, the passage configured to receive a sleeve of a trocar assembly therein, a release button movably coupled to the housing, the release button movable between an extended position and a compressed position, a spring disposed between the housing and the release button, the spring biasing the release button towards the extended position, a pin slidably disposed in a chamber of the housing, the pin slidable between an extended position and a retracted position, and a rocker arm operably coupling the pin and the release button such that moving the release button towards the compressed position causes the pin to slide towards the retracted position, the rocker arm pivotable about an axle extending through a center of the rocker arm.

A first end of the rocker arm may be pivotably coupled to the pin with a first spindle and a second end of the rocker arm may be coupled to the release button. Movement of the release button towards the compressed position may pivot the rocker arm about the axle such that the first end of the rocker arm pivots towards the passage and the second end of the rocker arms pivots away from the passage. The spring may be a leaf spring, a coil spring, or a two-axis spring. The second end of the rocker arm may be pivotably coupled to the release button with a second spindle.

In embodiments, a trocar release assembly for a surgical stapler includes a housing having opposed openings defining a passage therethrough, the passage configured to receive a sleeve of a trocar assembly therein, a release button movably coupled to the housing, the release button movable between an extended position and a compressed position, a spring disposed between the housing and the release button, the spring biasing the release button towards the extended position, a pin slidably disposed in a chamber of the housing, the pin slidable between an extended position and a retracted position, and a plate coupling the release button and the pin such that movement of the release button towards the compressed position slides the pin towards the retracted position, the plate slidable relative to the housing.

DESCRIPTION OF THE DRAWINGS

Embodiments of a surgical stapler are disclosed herein with reference to the drawings, wherein:

FIG. 25 is a perspective view of a fourth embodiment of a trocar release assembly;

FIG. 26 is an exploded view, with parts separated, of the trocar release assembly of FIG. 25;

FIG. 30 is an exploded view, with parts separated, of the trocar release assembly of FIG. 29;

FIG. 31 is a perspective view of a release assembly of the trocar release assembly of FIG. 29;

DETAILED DESCRIPTION

Embodiments of the presently disclosed trocar release assembly for a surgical stapler will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
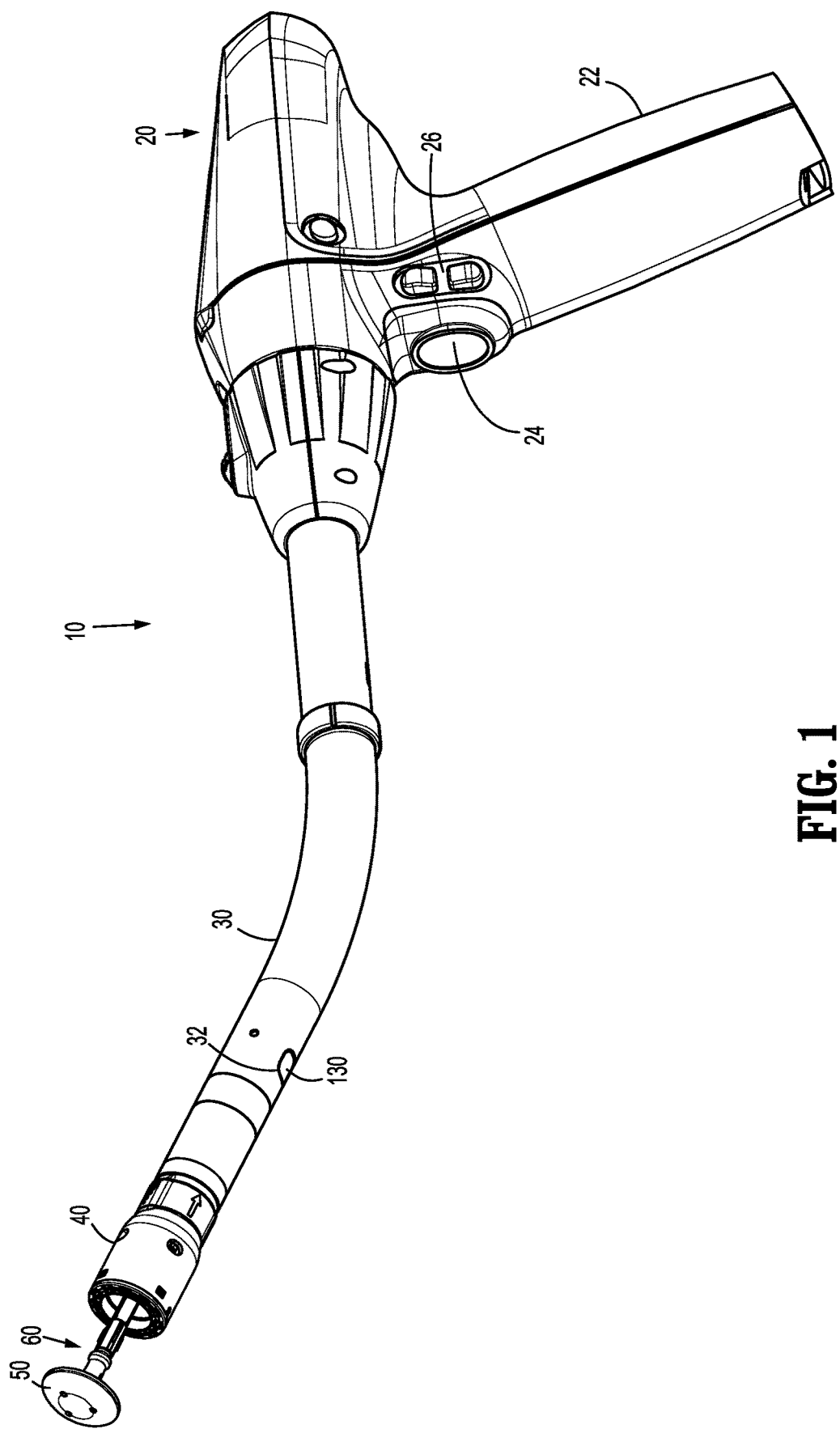
FIG. 1 is a perspective view of a surgical stapler according to an embodiment of the present disclosure.
Figure 2:
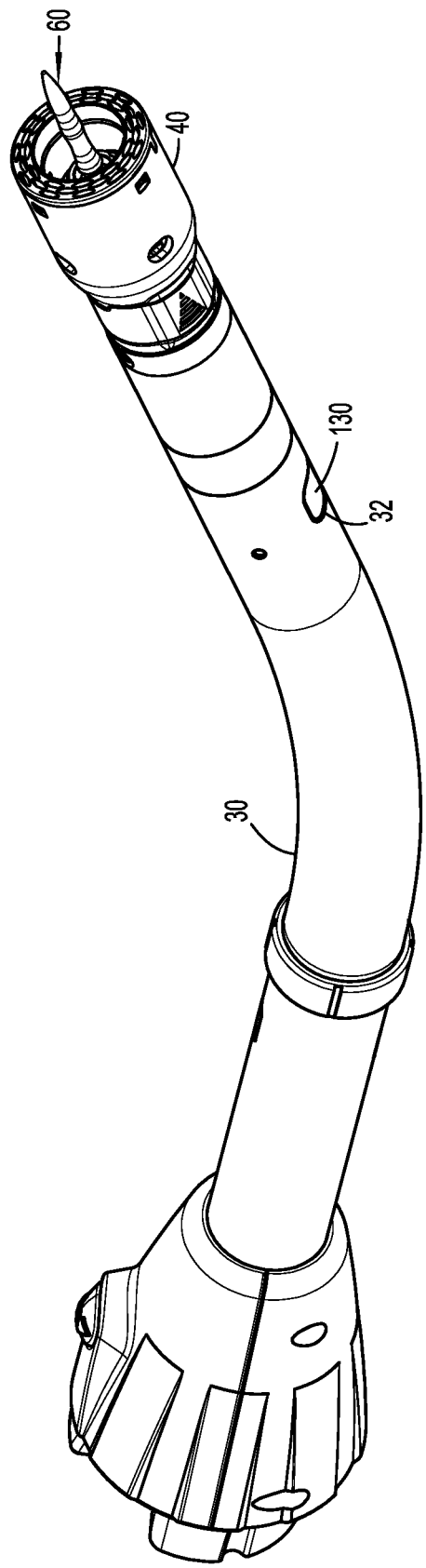
FIG. 2 is a perspective view of a tubular shaft of the surgical stapler of FIG. 1 with a distal portion of a trocar assembly extending from the tubular shaft.
Figure 3:
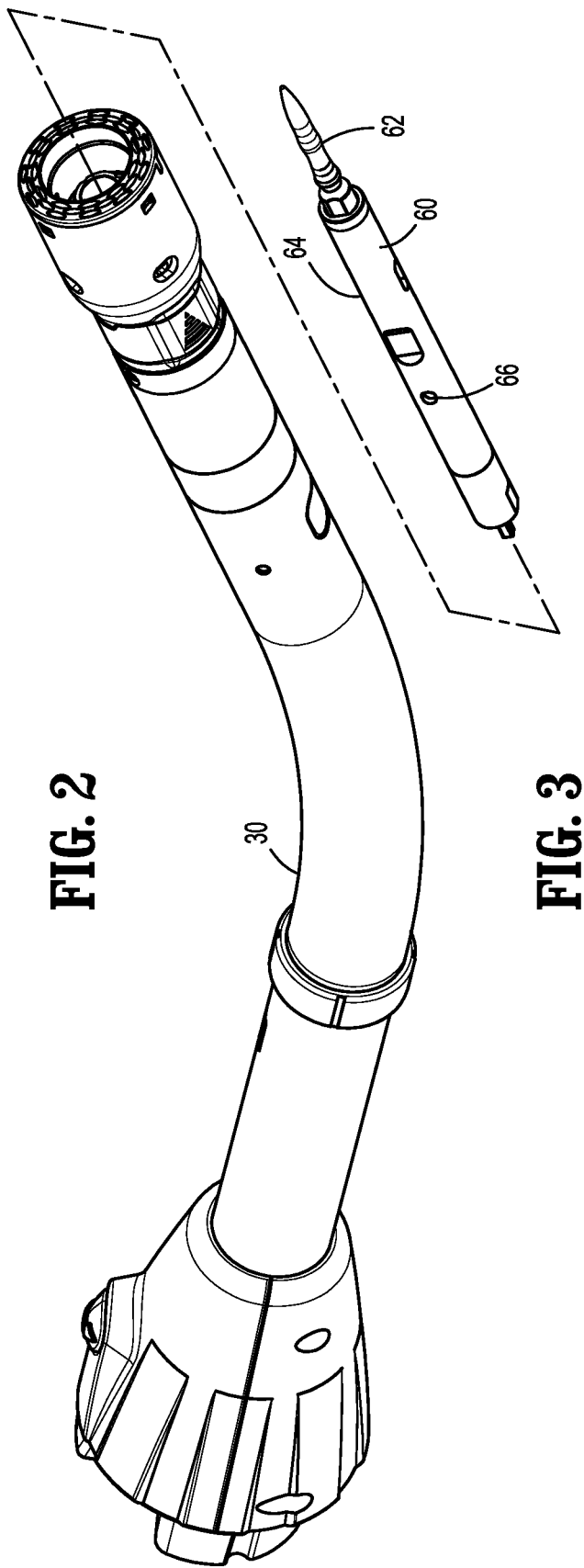
FIG. 3 is a perspective view of the tubular shaft of FIG. 2 with the trocar assembly shown separated from the tubular shaft.

Initially, with reference to FIGS. 1-3, a surgical stapler is shown and referenced generally as surgical stapler 10. The surgical stapler 10 is a circular stapler and includes a handle 20 assembly at one end and a tubular shaft 30 extending from the handle assembly 20. Although illustrated as a powered surgical stapler, surgical stapler 10 may be a manually operated instrument. The handle assembly 20 includes a power source (not shown) and buttons for operating the surgical stapler 10. A cartridge 40 is disposed at a distal end of the tubular shaft 30. The handle assembly 20 includes a fixed handle 22, an actuation button 24, and an approximation mechanism 26 for moving a trocar assembly 60 and an anvil 50 relative to the cartridge 40. The structure and function of handle assembly 20 will only be described herein to the extent necessary. It is envisioned that shell assembly may be used with any actuation assembly, powered or manual, and capable of two independent actuation strokes, for example. Commonly owned U.S. Pat. No. 8,806,973, the content of which is incorporated by reference herein in its entirety, discloses a surgical device having a powered actuator assembly including first and second drive members. In addition, it is envisioned that the independent actuation strokes may be completed by the same drive member completing two strokes or by two separate drive members. A trocar release assembly 100, as will be described in further detail hereinbelow, is located in the tubular shaft 30 and has a release button 130 that extends through a window 32 in the tubular shaft 30 for actuating the trocar release assembly 100. The trocar assembly 60 includes a trocar member 62 extending from a sleeve 64. The sleeve 64 includes one or more retention slots 66 for releasably coupling with the trocar release assembly 100 as will be described in further detail hereinbelow.

Figure 4:
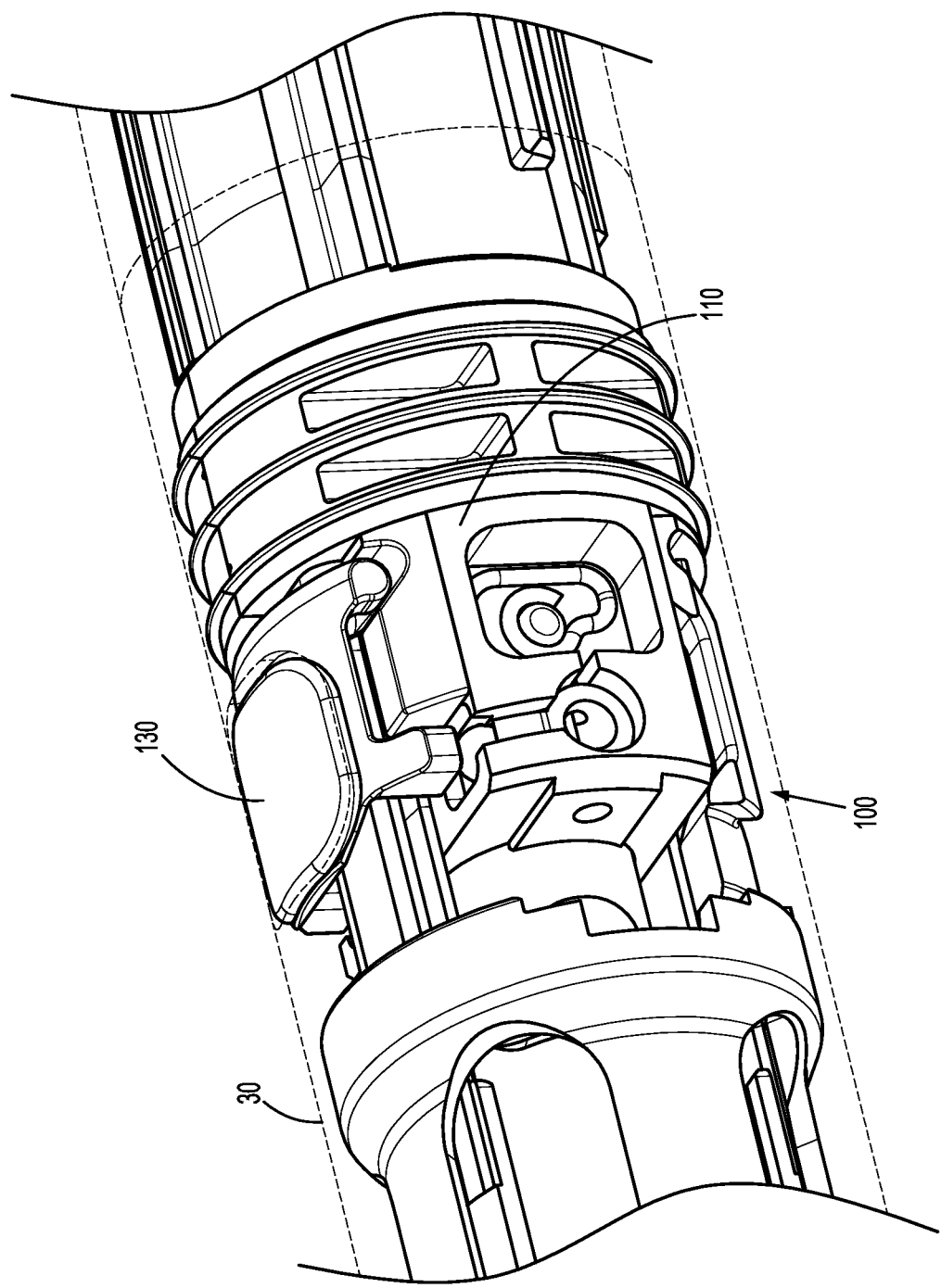
FIG. 4 is a side cut-away view of a portion of the tubular shaft of FIG. 2 illustrating a first embodiment of a trocar release assembly in a locked configuration.
Figure 5:
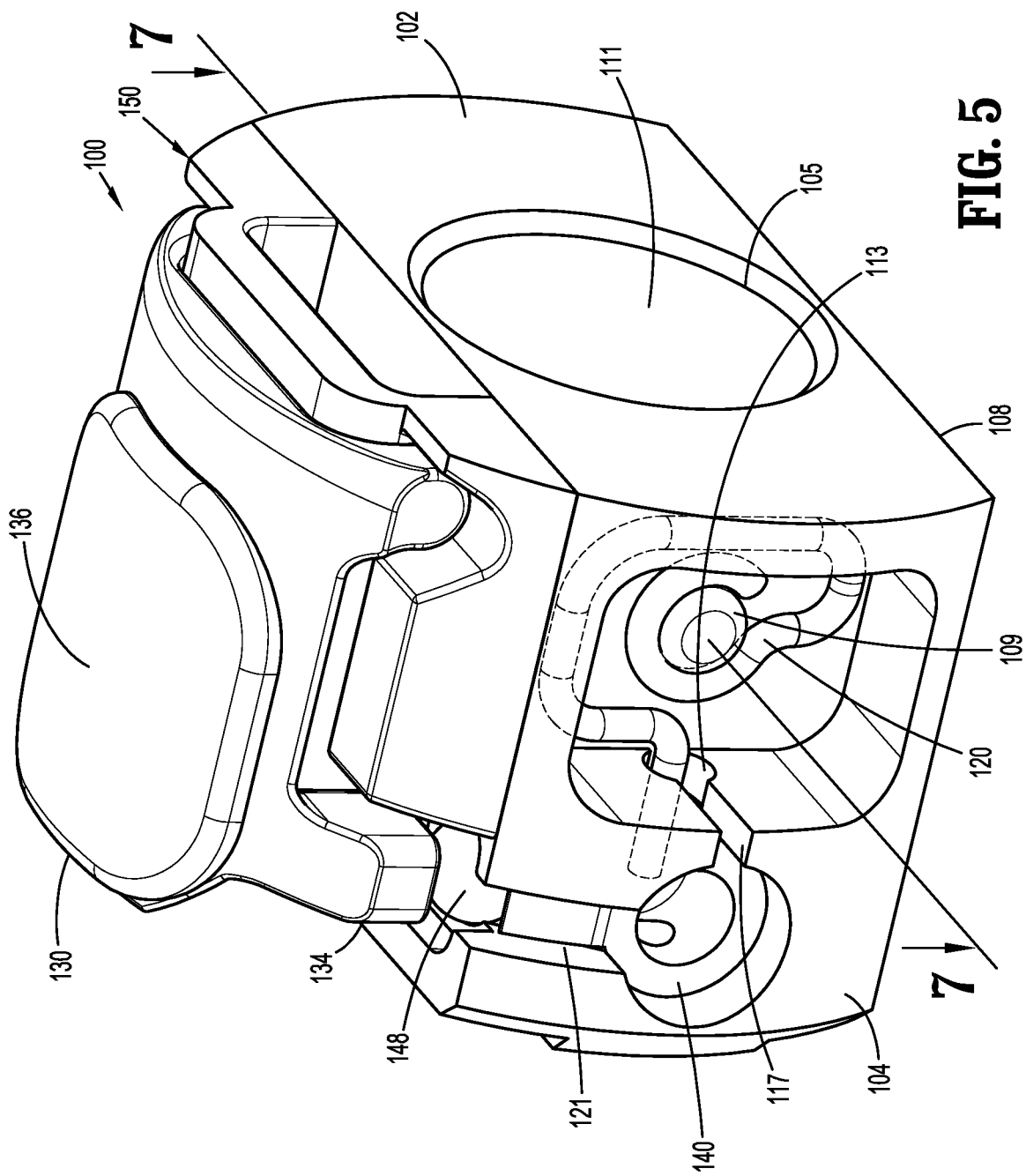
FIG. 5 is a perspective view of the trocar release assembly of FIG. 4.
Figure 6:
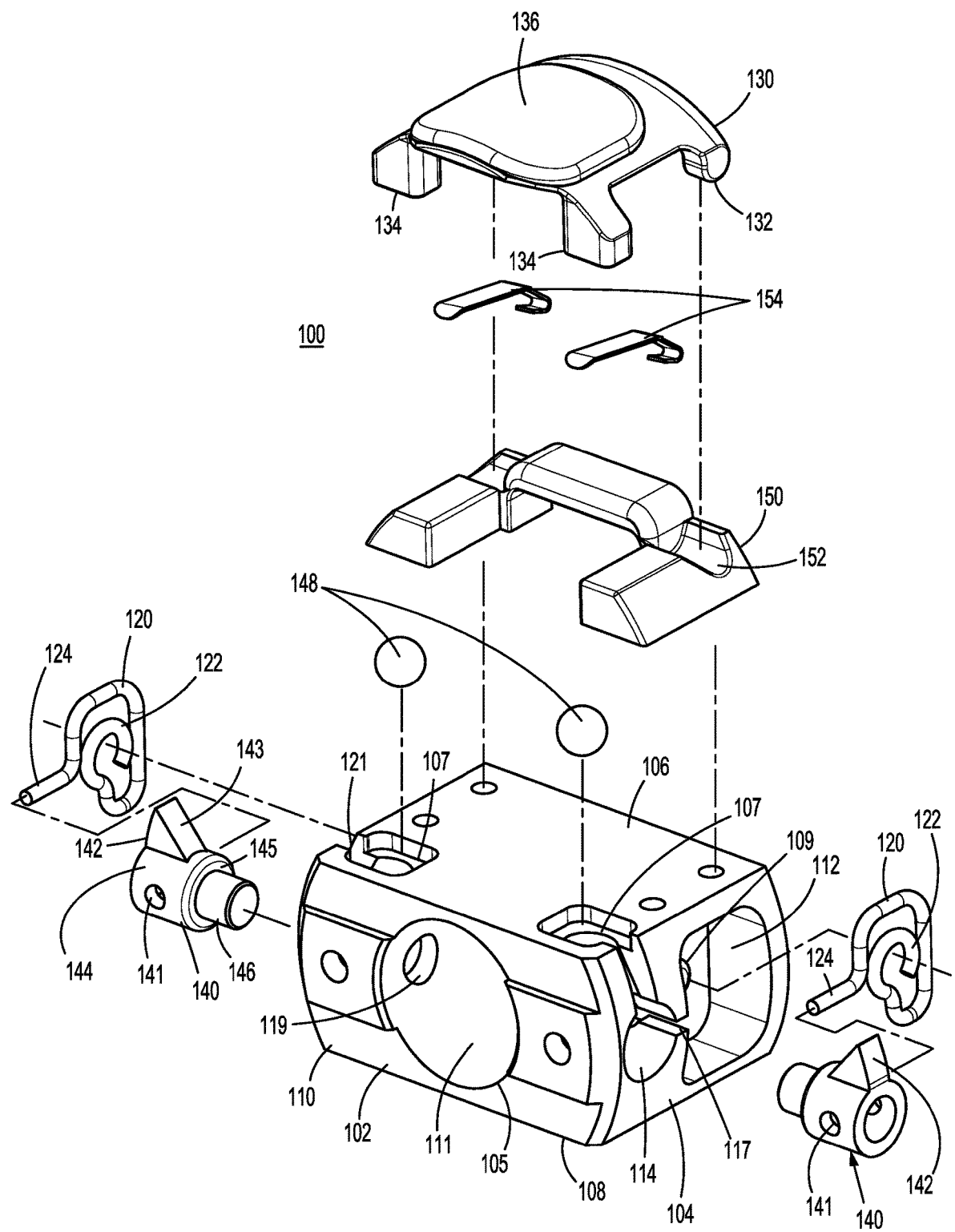
FIG. 6 is an exploded view, with parts separated, of the trocar release assembly of FIG. 5.

Referring now to FIGS. 4-6, a first embodiment of the trocar release assembly 100 is illustrated. The trocar release assembly 100 has a housing 110 with end faces 102, side faces 104, a top face 106, and a bottom face 108. As shown, the end faces 102, top face 106, and bottom face 108 are planar surfaces while the side faces 104 are arcuate surfaces. This arrangement allows the trocar release assembly 100 to reside within the circular profile of the tubular shaft 30 as shown in FIG. 4. Turning now to FIGS. 5 and 6, the end faces 102 have opposed openings 105 that define a passage 111 therebetween. A central longitudinal axis of the housing 110 extends through the passage 111 and is coaxially aligned with a central longitudinal axis of the tubular shaft 30. Each side face 104 includes a recess 112 supporting a spring 120 and a chamber 114 for slidably receiving a retention pin 140 therein. The springs 120 are formed from a suitable metal material (e.g., steel) that is normally disposed in a single plane. Each spring 120 has an eyelet 122 at one end and a prong 124 at the other end. The eyelets 122 are welded or otherwise secured to cylindrical protrusions 109 in the recesses 112 and securely attach the springs 120 to the housing 110. The prongs 124 extend from the recesses 112 through openings 113 in the recesses 112, into the chambers 114, and are received in orifices 141 of the retention pins 140. This arrangement biases the retention pins 140 towards an extended position such that distal portions 146 of the retention pins 140 extend into the passages 111 of the housing 110 via bores 119. Each orifice 141 is in communication with a slot 117 that opens at the side face 104 of the housing 110. The slots 117 are dimensioned for slidably receiving the prongs 124 of the springs 120 such that the prongs 124 can exit the orifices 141 and slide in the slots 117 as the retention pins 140 transition from the extended position to a retracted position where the distal portions 146 of the retention pins 140 are withdrawn from the passage 111 of the housing 110.

The distal portions 146 of the retention pins 140 have a diameter that is less than a diameter of main bodies 144 of the retention pins 140 defining shoulders 145 of the retention pins 140. It is contemplated that the distal portions 146 and the main bodies 144 may have the same diameter. The diameter of the distal portions 146 corresponds to a diameter of bores 119 of the housing 110 which allows the distal portions 146 of the retention pins 140 to enter the passage 111 of the housing 110. As the main bodies 144 of the retention pins 140 have a diameter greater than the diameter of the distal portions 146, the distance the retention pins 140 can travel towards the passage 111 is limited. The main bodies 144 of the retention pins 140 include the orifices 141 that receive the prongs 124 of the springs 120. The main bodies 144 of the retention pins 140 also include ramps 142 with sloped sections 143 that are slidable in notches 121 of the chambers 114 while the main bodies 144 of the retention pins 140 are slidable within the chambers 114.

Apertures 107 on the top face 106 of the housing 110 are sized to receive spheres 148. A frame 150 is attached to the top face 106 of the housing 110 for movably coupling the release button 130 to the housing 110. The release button 130 includes an outer surface 136 actuatable by a user. Feet 132 of the release button 130 are disposed in depressions 152 of the frame 150 and springs 154 (e.g., leaf springs) are attached to the frame 150 for biasing the release button 130 away from the top face 106 of the housing 110. The feet 132 are located on one end of the release button 130 and prongs 134 are located on the opposite end of the release button 130. The prongs 134 are in contact with the spheres 148 such that movement of the release button 130 towards the top face 106 of the housing 110 urges the spheres 148 towards the bottom face 108 of the housing 110. As the spheres 148 are in contact with the sloped sections 143 of the ramps 142, the spheres 148 move towards the bottom face 108 which causes the ramps 142 and the retention pins 140 to move away from the passage 111 of the housing 110 (i.e., outboard). The interaction between the spheres 148 and the sloped sections 143 of the ramps 142 slides the retention pins 140 away from the passage 111 against the bias of the springs 120 and transitions the retention pins 140 towards the retracted position. Once the release button 130 is fully depressed, the release button 130 will be at its closest position to the top face 106 of the housing 110 and the retention pins 140 will be fully retracted. Thus, the passage 111 through the housing 110 will be unobstructed and the sleeve 64 of the trocar assembly 60 (FIG. 3) is insertable into the passage 111 (see FIG. 9). This defines an unlocked configuration of the trocar release assembly 100.

Figure 7:
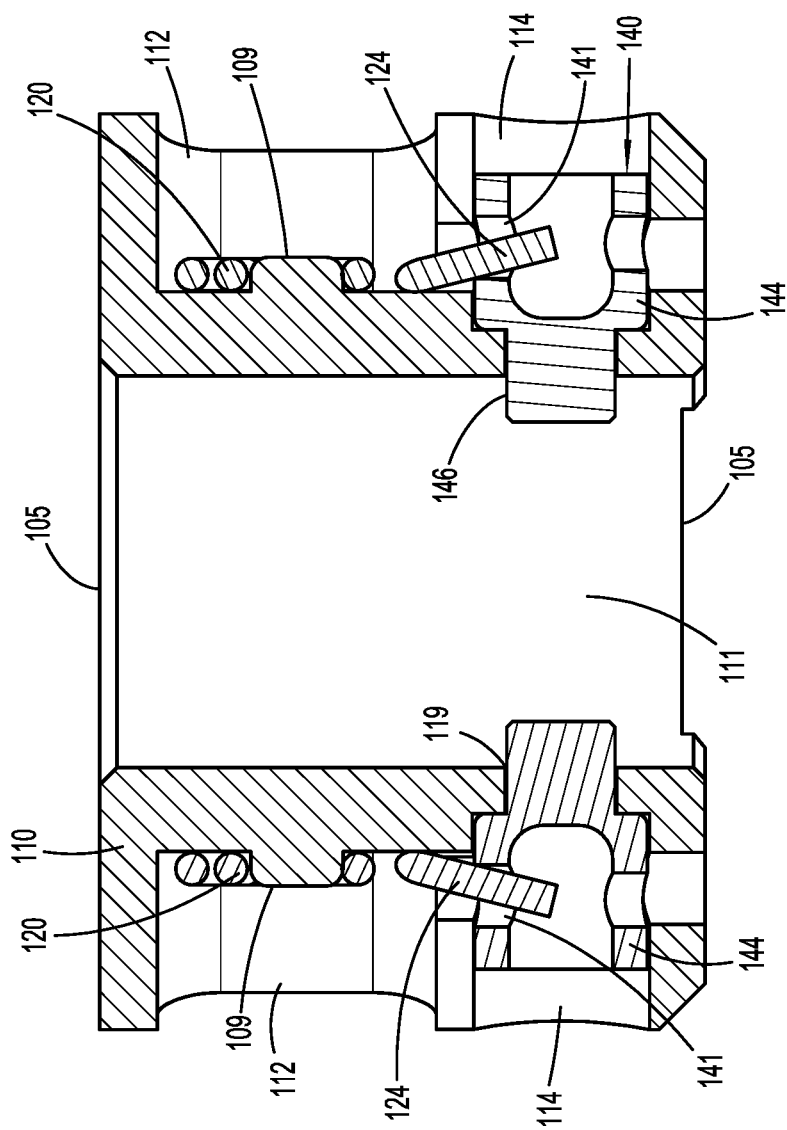
FIG. 7 is a cross-sectional view of the trocar release assembly taken along section line 7-7 of FIG. 5.
Figure 8:
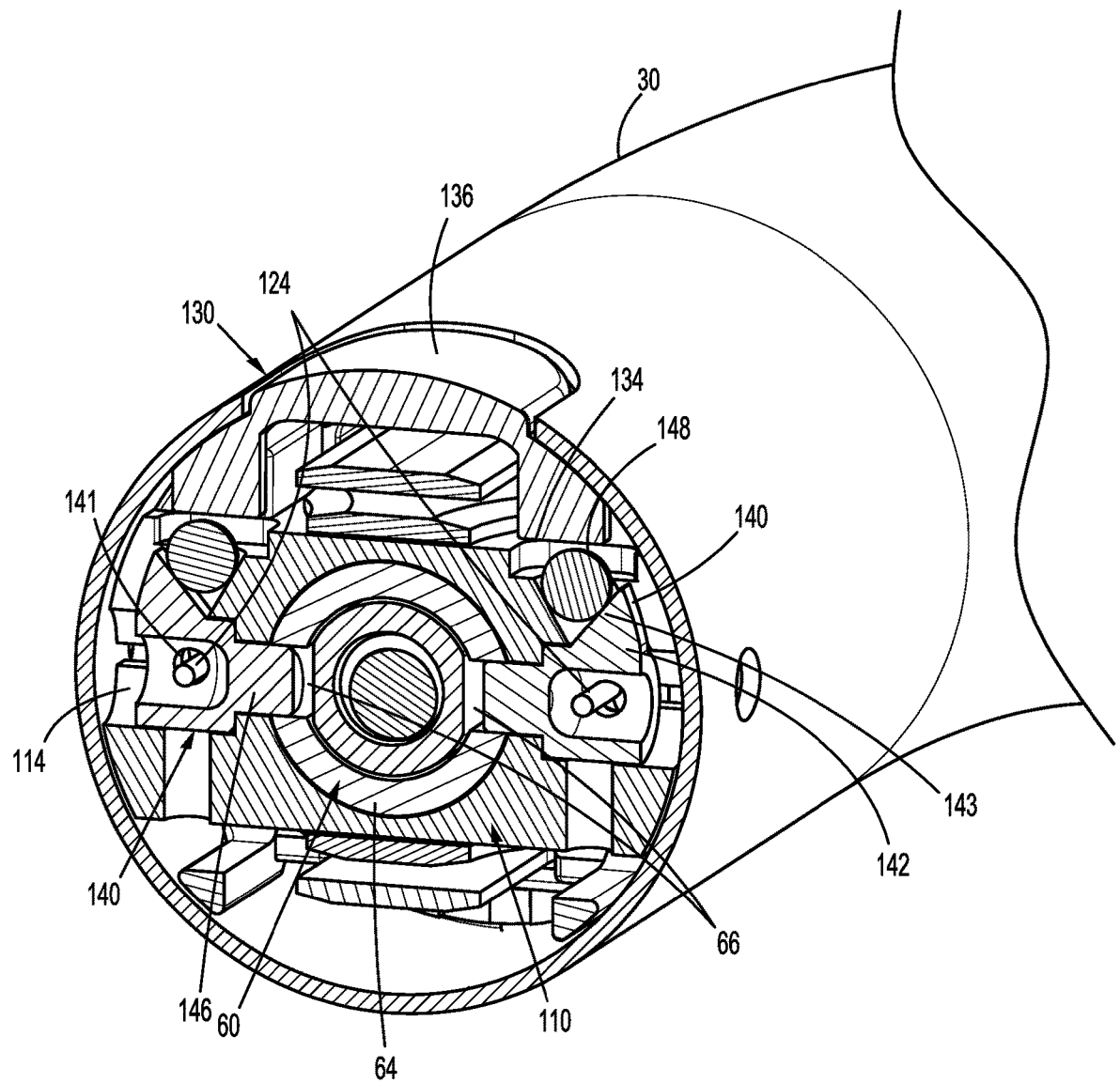
FIG. 8 is an end cross-sectional view of the tubular shaft of FIG. 2 showing the first embodiment of the trocar release assembly in the locked configuration.

With additional reference to FIGS. 7-9, operation of the trocar release assembly 100 will be discussed. FIG. 7 depicts a locked configuration of the trocar release assembly 100 in the absence of a trocar assembly 60 while FIG. 8 shows a locked configuration of the trocar release assembly 100 with the trocar assembly 60 secured therein. In the locked configuration, the retention pins 140 are fully extended such that their distal portions 146 protrude into the passage 111 for engaging the retention slots 66 of the sleeve 64 of the trocar assembly 60 that fixes the axial position of the trocar assembly 60 relative to the housing 110. This locks the trocar assembly 60 in the trocar release assembly 100 and inhibits inadvertent movement of the trocar assembly 60. In particular, the prongs 124 of the springs 120 extend through the orifices 141 of the main bodies 144 of the retention pins 140 and bias the retention pins 140 towards the passage 111 of the housing 110 (i.e., inboard) such that the distal portions 146 of the retention pins 140 are positioned in the retention slots 66 of the sleeve 64 of the trocar assembly 60, thereby securing the trocar assembly 60 to the housing 110 of the trocar release assembly 100.

Figure 9:
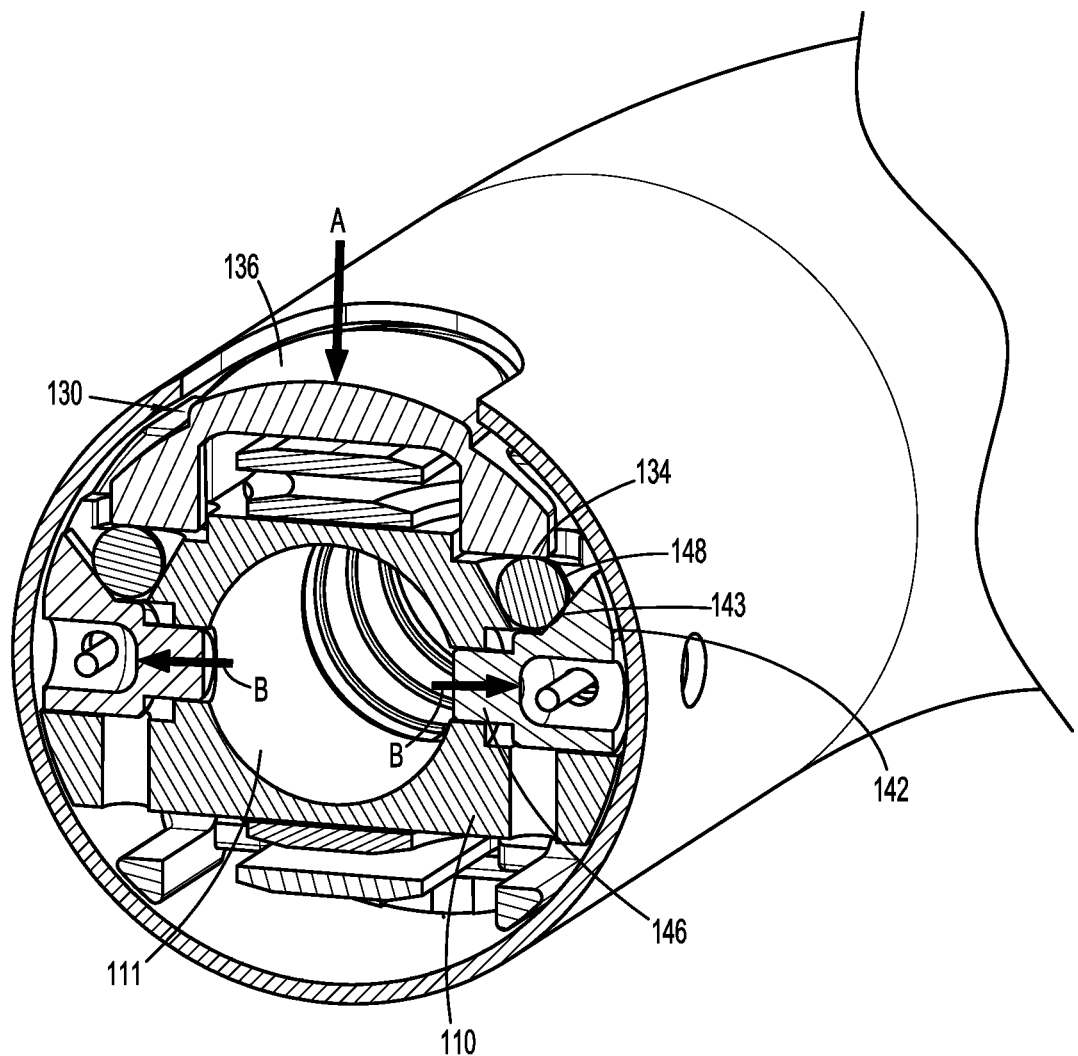
FIG. 9 is an end cross-sectional view of the tubular shaft of FIG. 2 showing the first embodiment of the trocar release assembly in an unlocked configuration.
Figure 10:
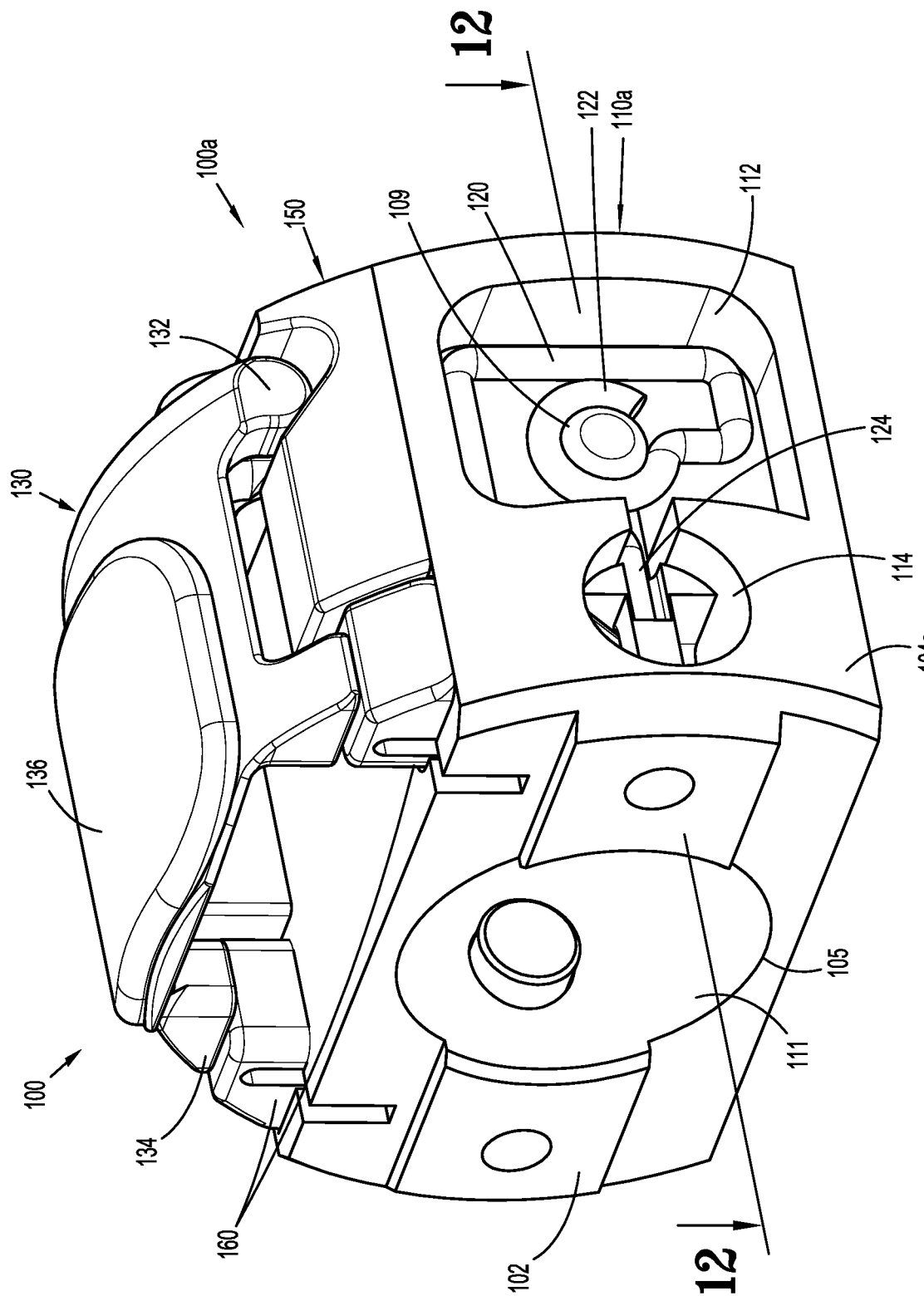
FIG. 10 is a perspective view of a second embodiment of a trocar release assembly.
Figure 11:
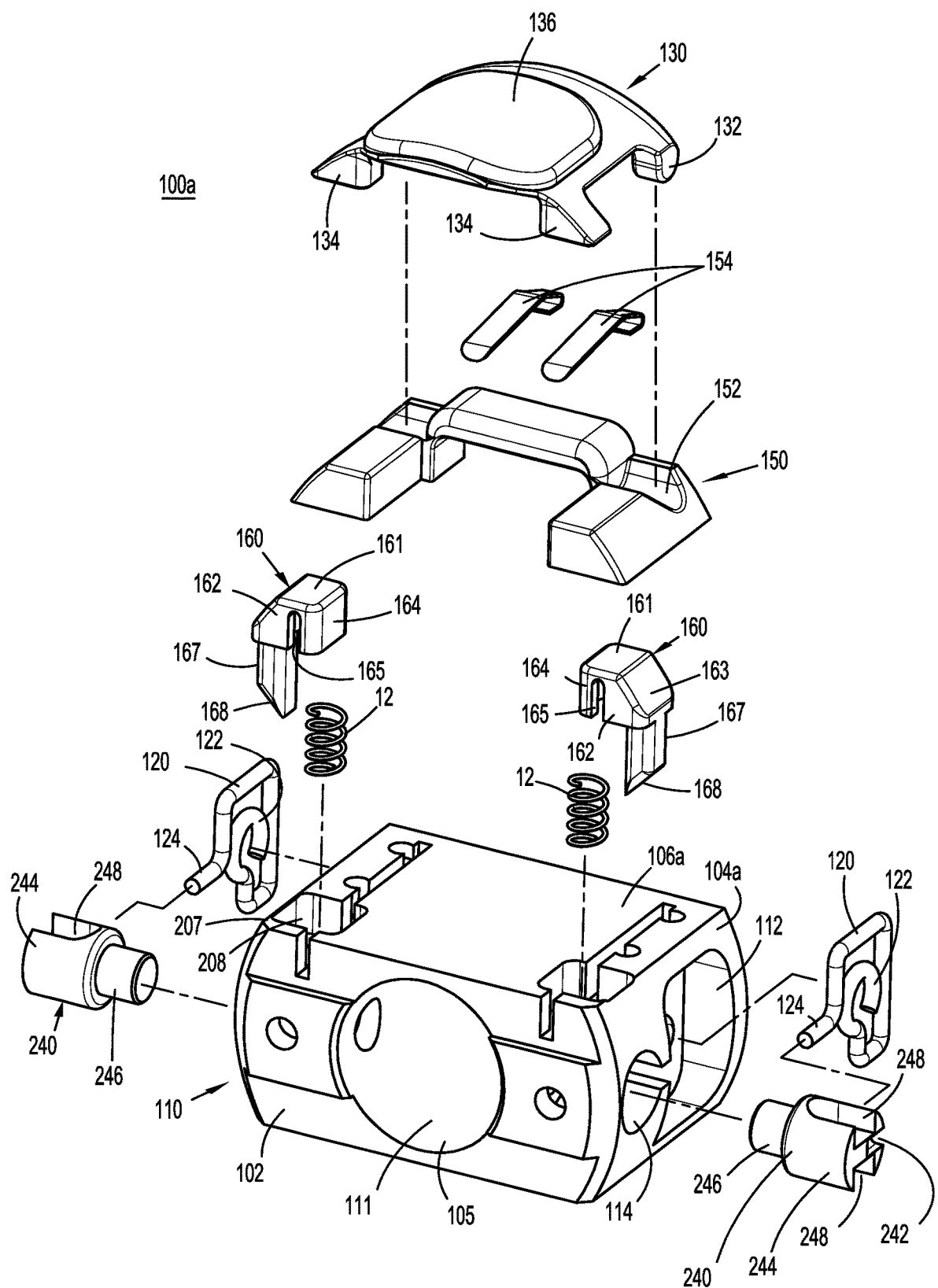
FIG. 11 is an exploded view, with parts separated, of the trocar release assembly of FIG. 10.
Figure 12:
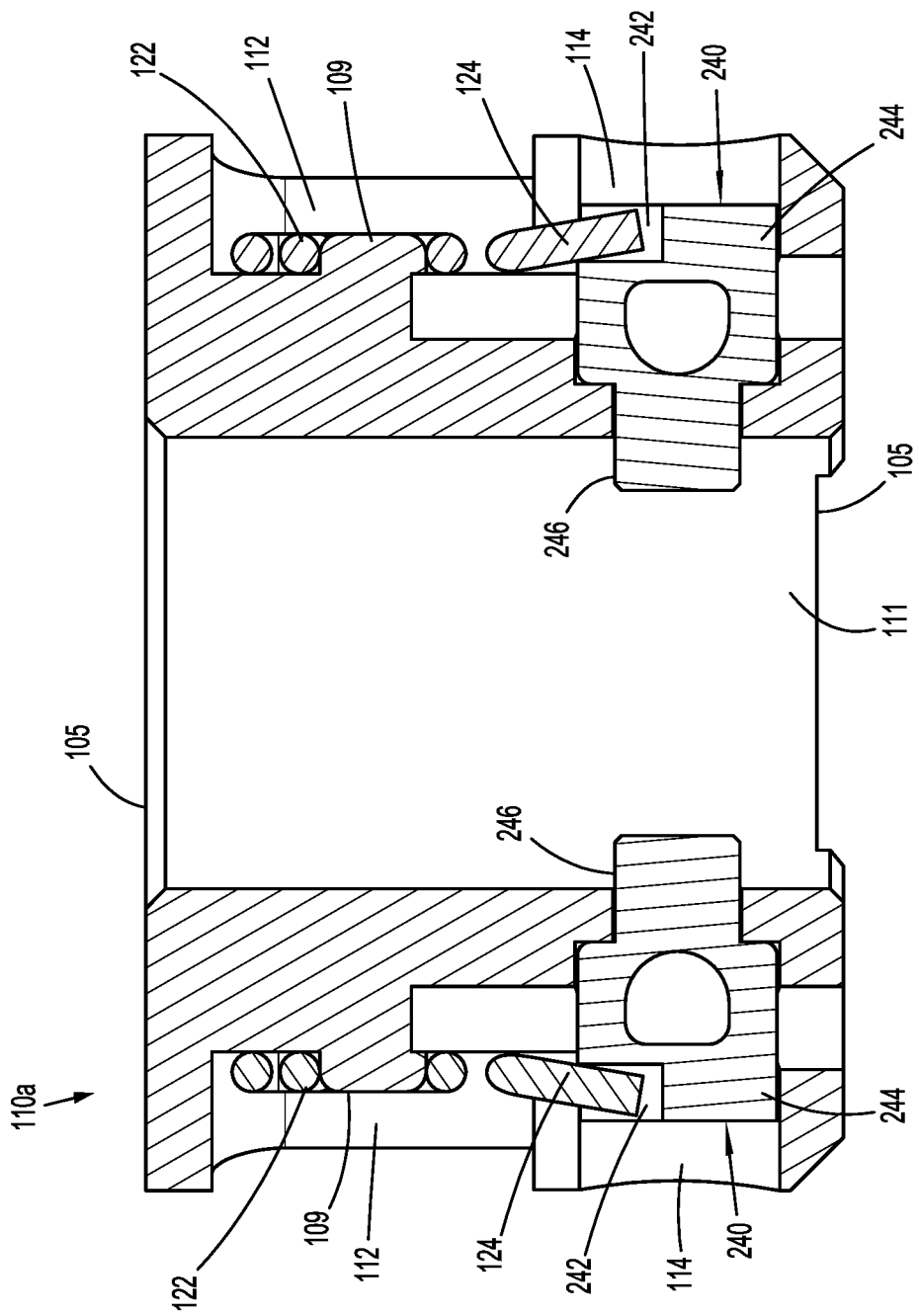
FIG. 12 is a cross-sectional view of the trocar release assembly taken along section line 12-12 of FIG. 10.
Figure 13:
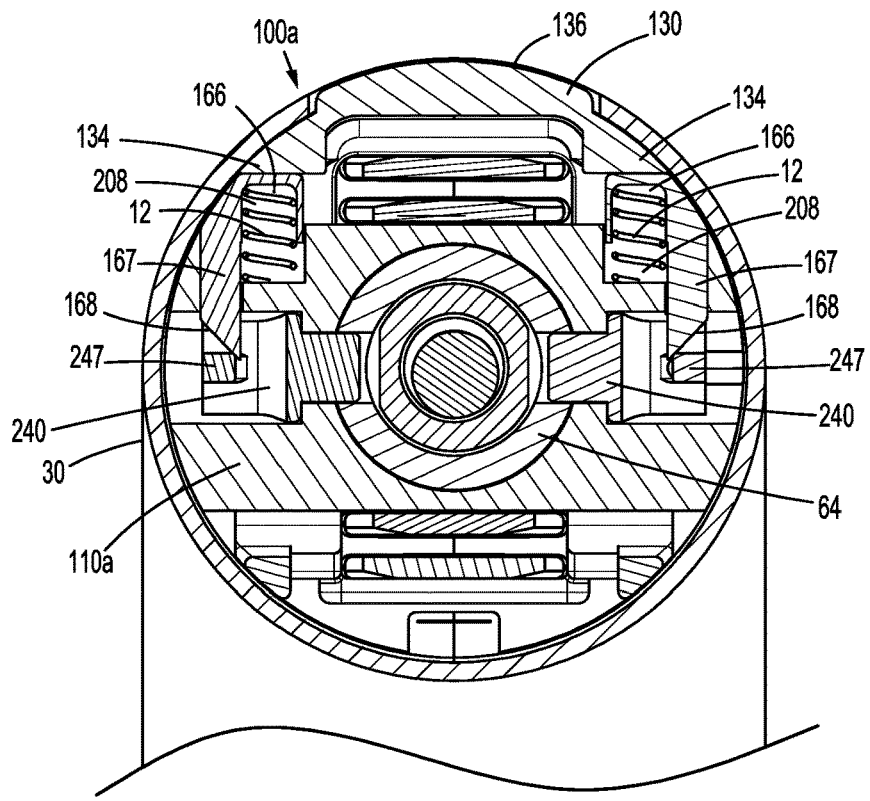
FIG. 13 is an end cross-sectional view of the tubular shaft of FIG. 2 showing the second embodiment of the trocar release assembly in a locked configuration.
Figure 14:
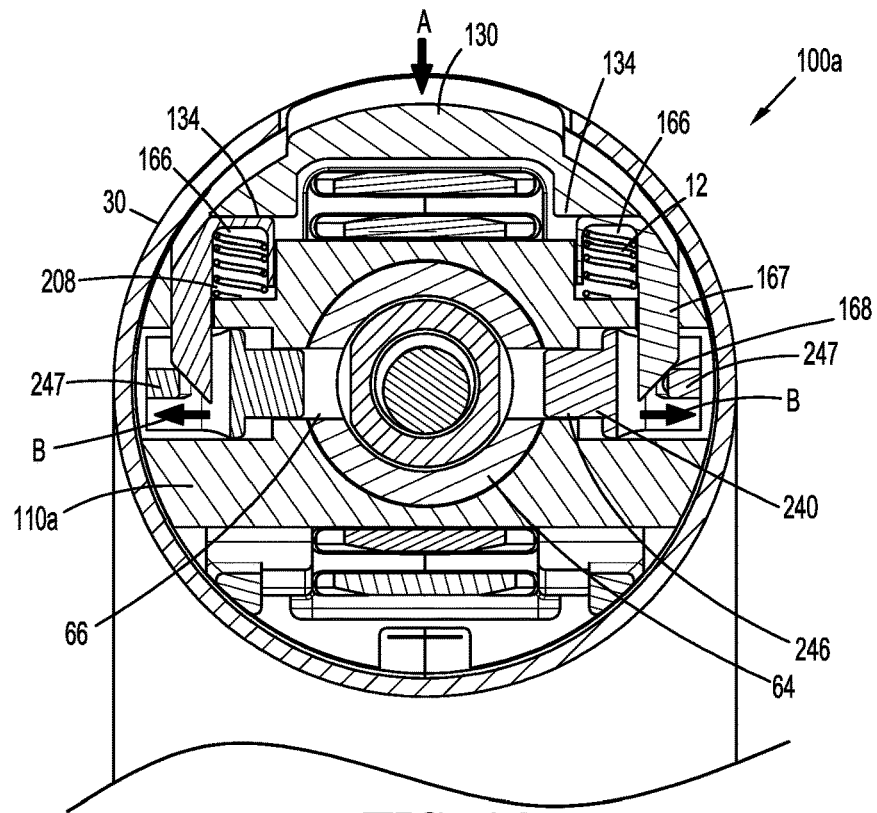
FIG. 14 is an end cross-sectional view of the tubular shaft of FIG. 2 showing the second embodiment of the trocar release assembly in an unlocked configuration.
Figure 15:
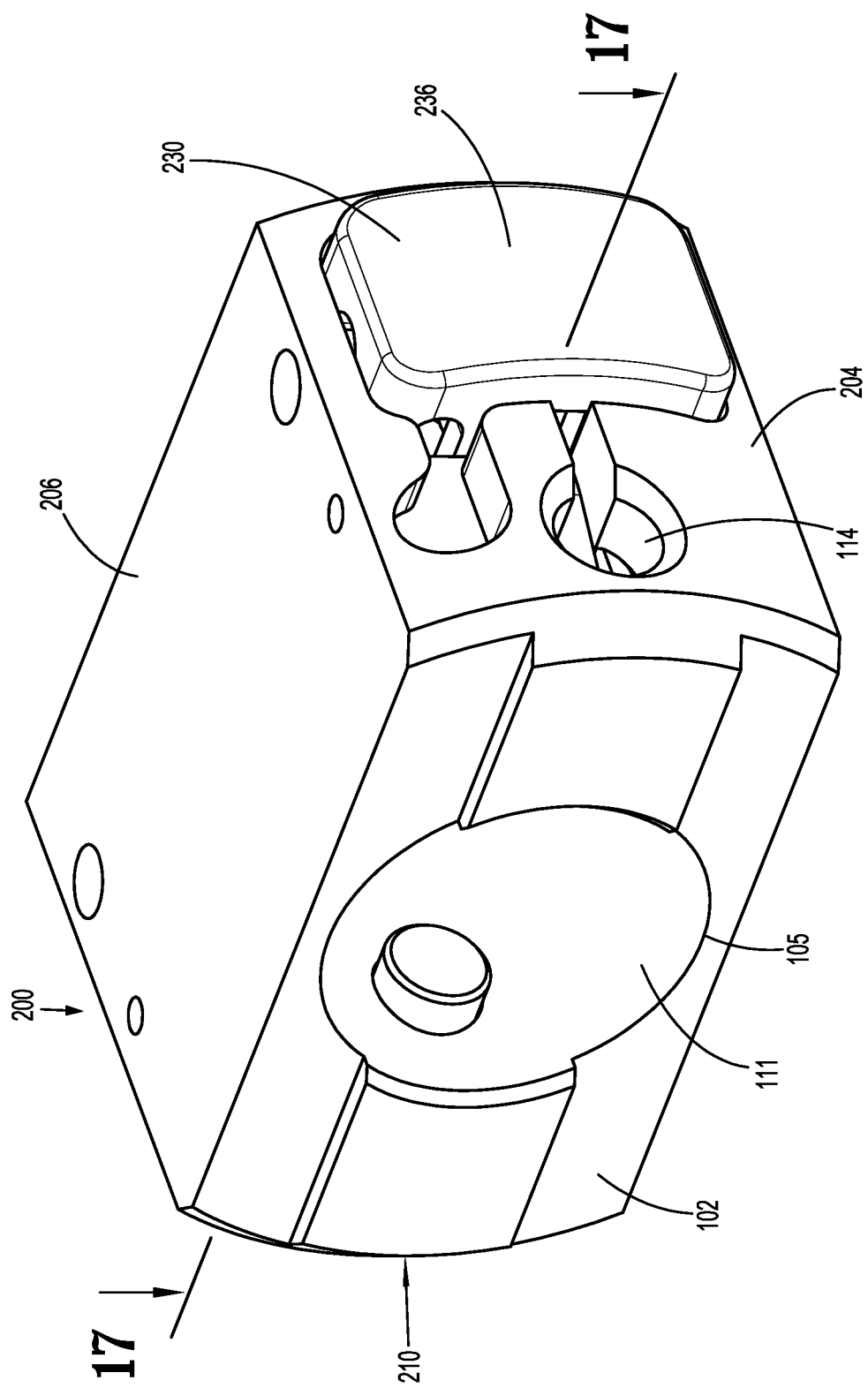
FIG. 15 is a perspective view of a third embodiment of a trocar release assembly
Figure 16:
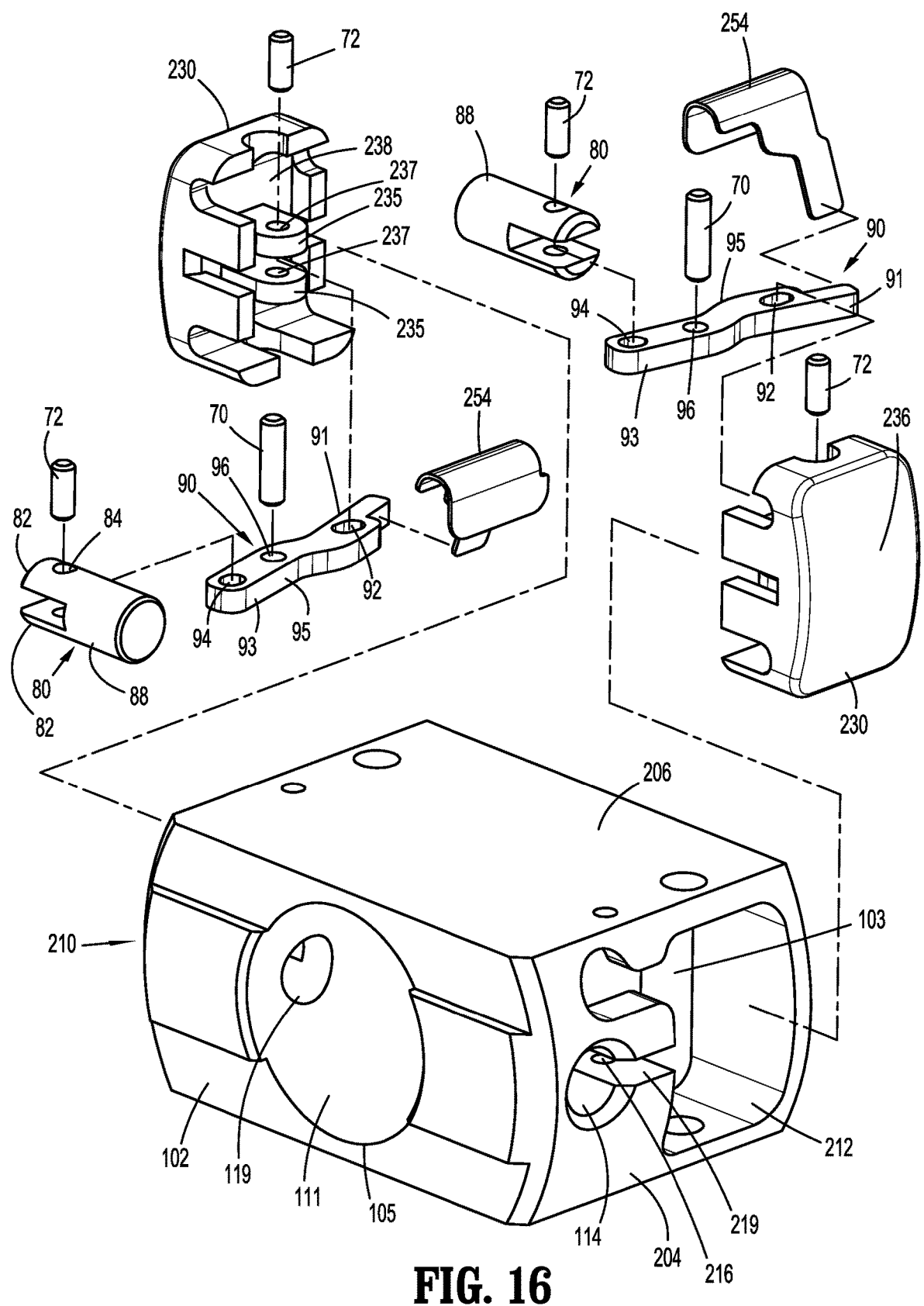
FIG. 16 is an exploded view, with parts separated, of the trocar release assembly of FIG. 15 with leaf springs.
Figure 17:
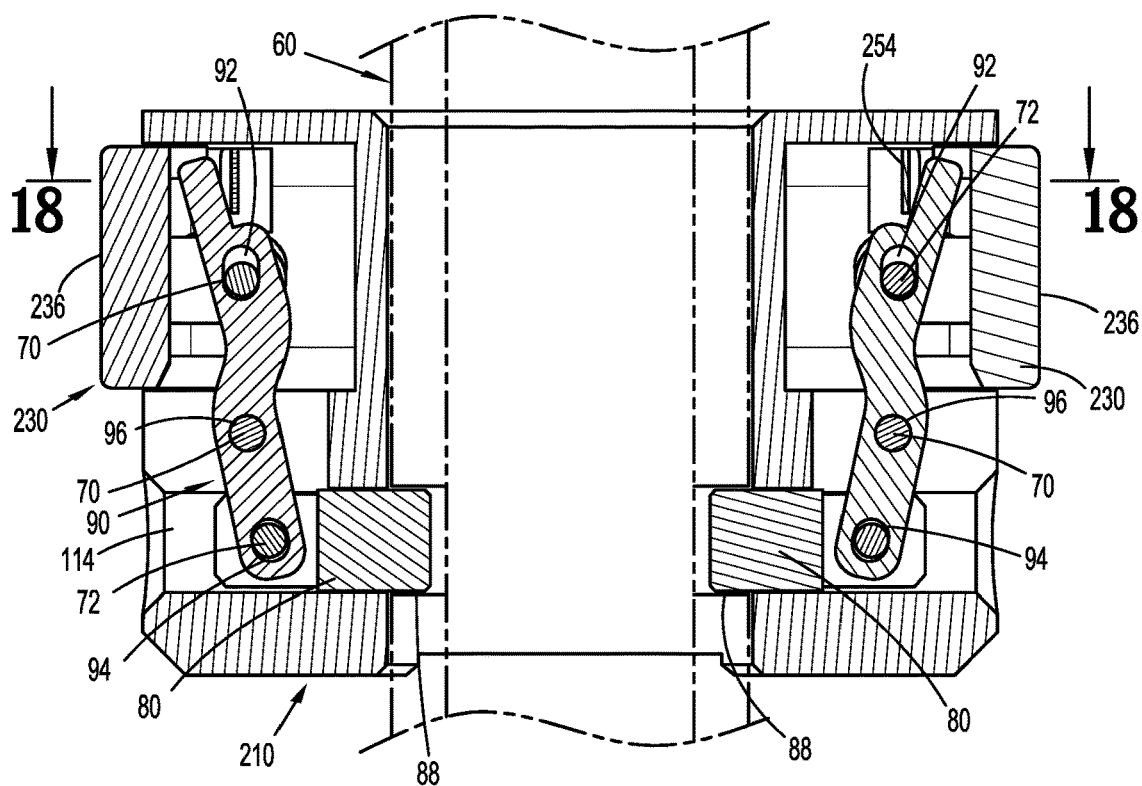
FIG. 17 is a cross-sectional view of the trocar release assembly taken along section line 17-17 of FIG. 15 in a locked configuration.
Figure 18:
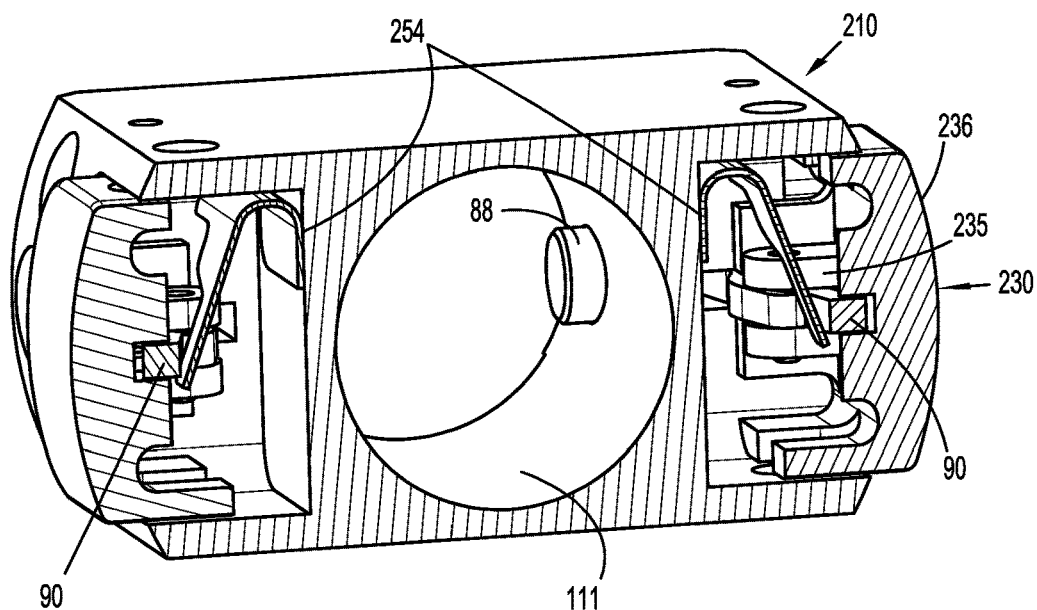
FIG. 18 is a cross-sectional view of the trocar release assembly taken along section line 18-18 of FIG. 17.
Figure 19:
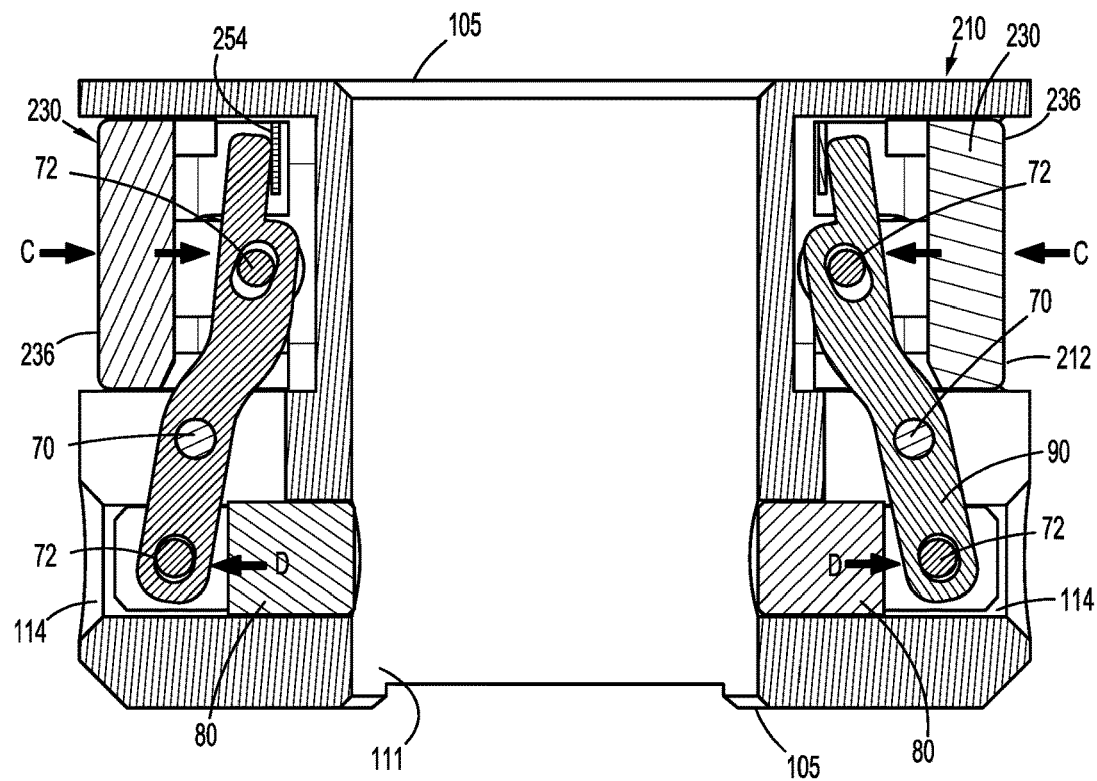
FIG. 19 is a cross-sectional view of the trocar release assembly of FIG. 15 in an unlocked configuration.

Turning now to FIG. 9, the trocar release assembly 100 is shown in an unlocked configuration and the trocar assembly 60 has been removed from the trocar release assembly 100. The release button 130 has been moved (i.e., depressed) in the direction of arrow "A" to a position where it is at its closest position to the top face 106 of the housing 110 (i.e., compressed position). As release button 130 is moved in the direction of arrow "A", the prongs 134 of the release button 130 also move in the same direction causing the spheres 148 to slide along the sloped sections 143 of the ramps 142 of the retention pins 140. This causes the retention pins 140 to move in the direction of arrow "B" and retract the distal portions 146 of the retention pins 140 from the retention slots 66 in the sleeve 64 of the trocar assembly 60 (FIG. 8). With the retention pins 140 fully retracted from the passage 111 of the housing 110, the trocar release assembly 100 is in the unlocked configuration which allows for insertion and/or removal of the trocar assembly 60. Once the release button 130 is released, the springs 154 (FIG. 6) will urge the release button 130 back towards the extended position. As force has been removed from the spheres 148, the biasing action of the springs 120 (FIG. 7) urges the retention pins 140 in an inboard direction towards their extended positions. Once the retention pins 140 are fully extended, the distal portions 146 of the retention pins 140 protrude into the passage 111 (FIG. 7) and prevent insertion and/or removal of trocar assembly 60 into the housing 110 since the outside diameter of the sleeve 64 of the trocar assembly 60 is greater than the distance between the distal portions 146 of the retention pins 140.

Referring now to FIGS. 10-14, another embodiment of the trocar release assembly is shown and identified as trocar release assembly 100a. The trocar release assembly 100a is similar to the trocar release assembly 100 discussed hereinabove and the following discussion will focus of the differences therebetween. As in the previous embodiment, the trocar release assembly 100a includes a housing 110a defining a passage 111 therethrough, a frame 150 attached to a top face 106a of the housing 110a, a release button 130, and springs 154 attached to the frame 150. The release button 130 includes an outer surface 136 actuatable by a user. Additionally, the housing 100a has recesses 112 on the side faces 104a for receiving springs 120 that bias retention pins 240 disposed in chambers 114 of the housing 110a. In this embodiment, each retention pin 240 has a distal portion 246 with a first diameter and a body 244 with a second diameter that is greater than the first diameter that defines shoulders 245 of the retention pins 240. Rather than including orifices in the bodies 244, the retention pins 240 include notches 242 for receiving the prongs 124 of the springs 120 such that the springs 120 bias the retention pins 240 towards the passage 111 of the housing 110a (i.e., inboard) and the extended position of the retention pins 240. The bodies 244 of the retention pins 240 also include top and bottom cavities 248 that are orthogonal to the notches 242. The cavities 248 extend substantially along lengths of the bodies 244 of the retention pins 240 and are configured to slidably receive distal tips 168 of legs 167 of cam plungers 160. The cam plungers 160 are slidably disposed in pockets 208 of the housing 110a which have openings 207 on the top face 106a of the housing 110a. Each cam plunger 160 includes a body portion 162 from which the leg 167 extends. A top surface 161 of the body portion 162 is planar and the body portion 162 also includes a sloped surface 163 extending at an acute angle from the planar top surface 161 and a wall 164 extending orthogonally to the top surface 161. The body portion 162 also includes a slit 165 extending parallel to the wall 164 and a nook 166 (FIG. 13) defined between the wall 164 and the sloped surface 163 for receiving a portion of a spring 12 (i.e., coil spring). The spring 12 biases the cam plunger 160 away from the bottom face 108 of the housing 110a. The distal tip 168 of the leg 167 is angled and defines an acute angle extending in the opposite direction of the acute angle of the sloped surface 163. The distal tip 168 of the leg 167 is configured to engage a shelf 247 (FIG. 13) in the body 244 of the retention pin 240. When the release button 130 is actuated (i.e., depressed), the prongs 134 of the release button 130 engage the top surfaces 161 of the cam plungers 160 overcoming the bias of the springs 120 such that the release button 130 and the cam plungers 160 move towards the bottom face 108 of the housing 110a. As the cam plungers 160 move towards the bottom face 108, the angled surface of the distal tip 168 cams against the edge of the shelf 247 urging the retention pin 240 away from the passage 111 of the housing 110a (i.e., outboard) such that the retention pin 240 transitions to the retracted position and the distal portion 246 of the retention pin 240 is withdrawn from the passage 111 of the housing 110a. This defines the unlocked configuration of the trocar release assembly 100a.

Turning now to FIGS. 15-28, another embodiment of the trocar release assembly is shown and identified as trocar release assembly 200. The trocar release assembly 200 includes a housing 210 similar to the housing 110 with the main differences being side and top faces 204, 206. As in the previous embodiments, the housing 210 includes a passage 111 therethrough that extends between the end faces 102 and the passage 111 includes bores 119 for slidably receiving distal portions 88 of retention pins 80. Each side face 204 includes a recess 212 that is configured to slidably receive a release button 230 therein. Additionally, each side face 204 includes a chamber 114 for slidably receiving the retention pin 80 and a slot 219 that extends between the recess 212 and the chamber 114. The slot 219 includes opposed openings 216 for receiving a pivot pin 70 that pivotably couples a rocker arm 90 with the side face 204 of the housing 210. Each release button 230 includes an outer surface 236 actuatable by a user. An inner surface 238 of each release button 230 has projections 235 that extend substantially perpendicular to the inner surface 238 and each projection 235 includes a bore 237 with the bores 237 being coaxially aligned for receiving a pin 72 therethrough. A first section 91 of the rocker arm 90 has an oblong hole 92 extending therethrough and is disposed between the projections 235 of the release button 230 such that the oblong hole 92 of the rocker arm 90 is aligned with the bores 237 of the projections 235 such that pin 72 is insertable into the oblong hole 92 and the bores 237 to couple the release button 230 and the rocker arm 90 together. A second section 93 of the rocker arm 90 also includes an oblong hole 94 extending therethrough and is disposed between fingers 82 of the retention pin 80 such that the oblong hole 94 of the rocker arm 90 is aligned with opposed openings 84 of the fingers 82 such that the pin 72 is insertable into the oblong hole 94 and openings 84 to couple the retention pin 80 to the rocker arm 90. In this embodiment, the retention pin 80 has a substantially uniform outer diameter that is slidable through the bore 119 such that the distal portion 88 of the retention pin 80 extends into the passage 111 and defines the extended position of the retention pin 80. A leaf spring 254 is positioned between a wall 103 of the recess 212 and a surface of the second section 93 of the rocker arm 90 for biasing the rocker arm 90 and the release button 230 towards the extended position. The rocker arm 90 is pivotable about the pivot pin 70 that is disposed in the bore 96 of the center section 95. As the release button 230 is operatively coupled to the retention pin 80, when the release button 230 is in the extended position the retention pin 80 is in the extended position and the trocar release assembly 200 is in a locked configuration. Depressing the release button 230 in the direction of arrow "C" overcomes the bias of the leaf spring 254 and pivots the rocker arm 90 such that the first section 91 is closer to the wall 103 of the recess (i.e., inboard) and the second section 93 moves away from the passage 111 of the housing 210 (i.e., outboard) in the direction of arrow "D", which retracts the distal portion 88 of the retention pin 80 out of the passage 111 thereby defining the unlocked configuration of the trocar release assembly 200. One end of the leaf spring 254 may be welded to the wall 103 of recess 212.

Figure 20:
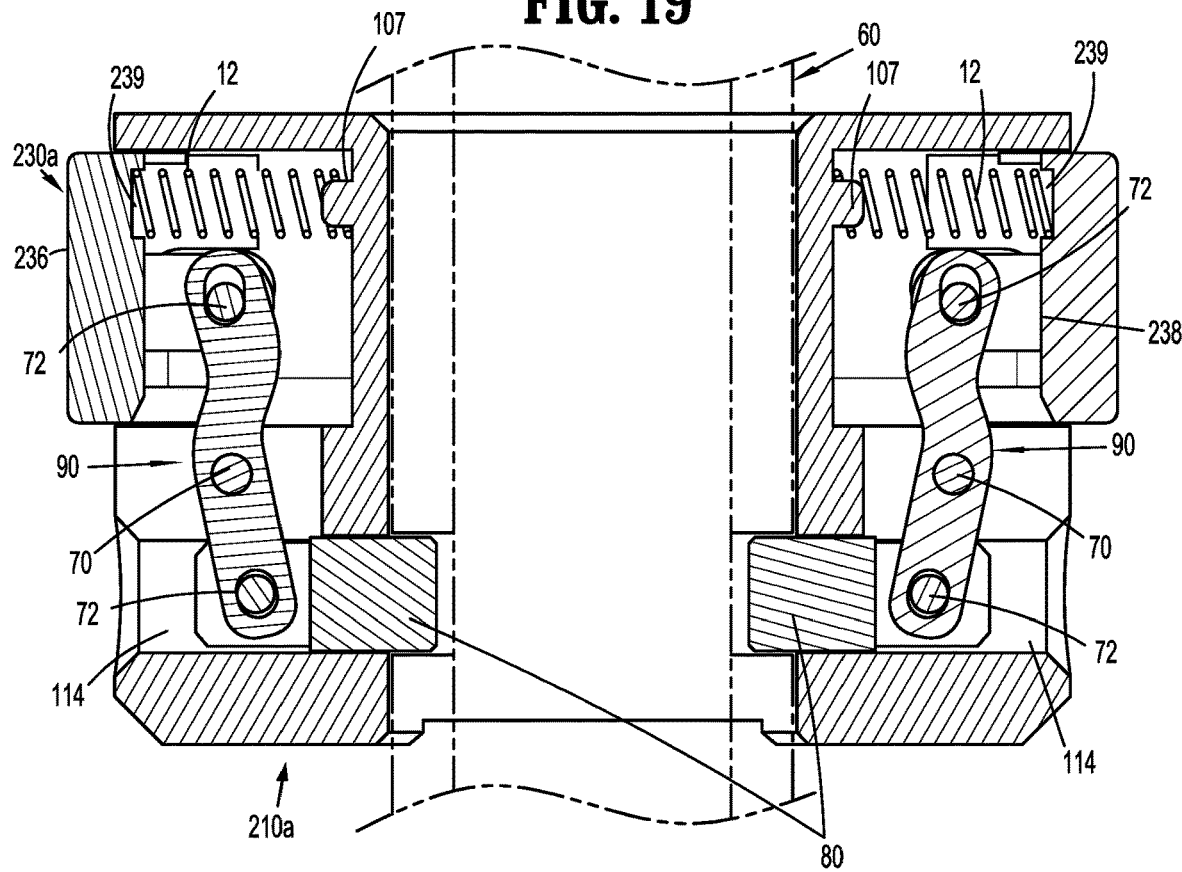
FIG. 20 is a cross-sectional view of the trocar release assembly of FIG. 15 in a locked configuration with coil springs.
Figure 21:
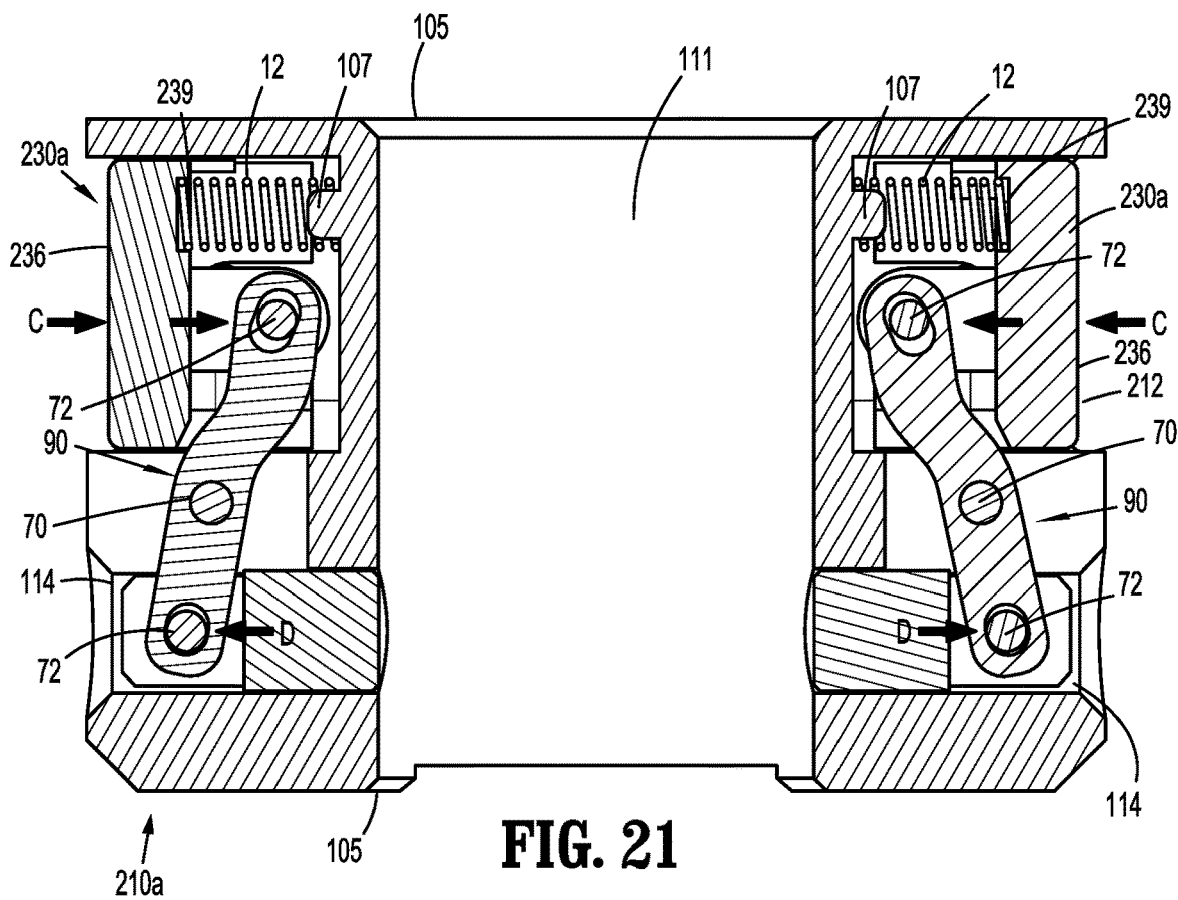
FIG. 21 is a cross-sectional view of the trocar release assembly of FIG. 20 in an unlocked configuration.

With additional reference to FIGS. 20 and 21, a further embodiment of the trocar release assembly is illustrated and identified as trocar release assembly 200a. In this modification of the embodiment of FIGS. 15-18, the leaf spring 254 is replaced with coil spring 12. The coil spring 12 extends between the wall 103 of the recess 212 and the inner surface 238 of the release button 230a. One end of the coil spring 12 is positioned over a stud 107 on the wall 103 of the recess 212 and the other end of the coil spring 12 is positioned in a cut-out 239 of the inner surface 238 of the release button 230a. In this configuration, the coil spring 12 biases the release button 230a towards the extended position (i.e., outboard) such that the first section 91 of the rocker arm 90 pivots away from the wall 103 of the recess 212 and the second section 93 of the rocker arm 90 pivots towards the passage 111 of housing 210a (i.e., inboard) thereby sliding the retention pin 80 towards the extended position and defining the locked configuration of the trocar release assembly 200a. As in the previous embodiment, depressing the release button 230a in the direction of arrow "C" overcomes the bias of the coil spring 12 and pivots the rocker arm 90 such that the first section 91 is closer to the wall 103 of the recess (i.e., inboard) and the second section 93 moves away from the passage 111 of the housing 210a (i.e., outboard), which retracts the distal portion 88 of the retention pin 80 out of the passage 111 in the direction of arrow "D" thereby defining the unlocked configuration of the trocar release assembly 200a.

Figure 22:
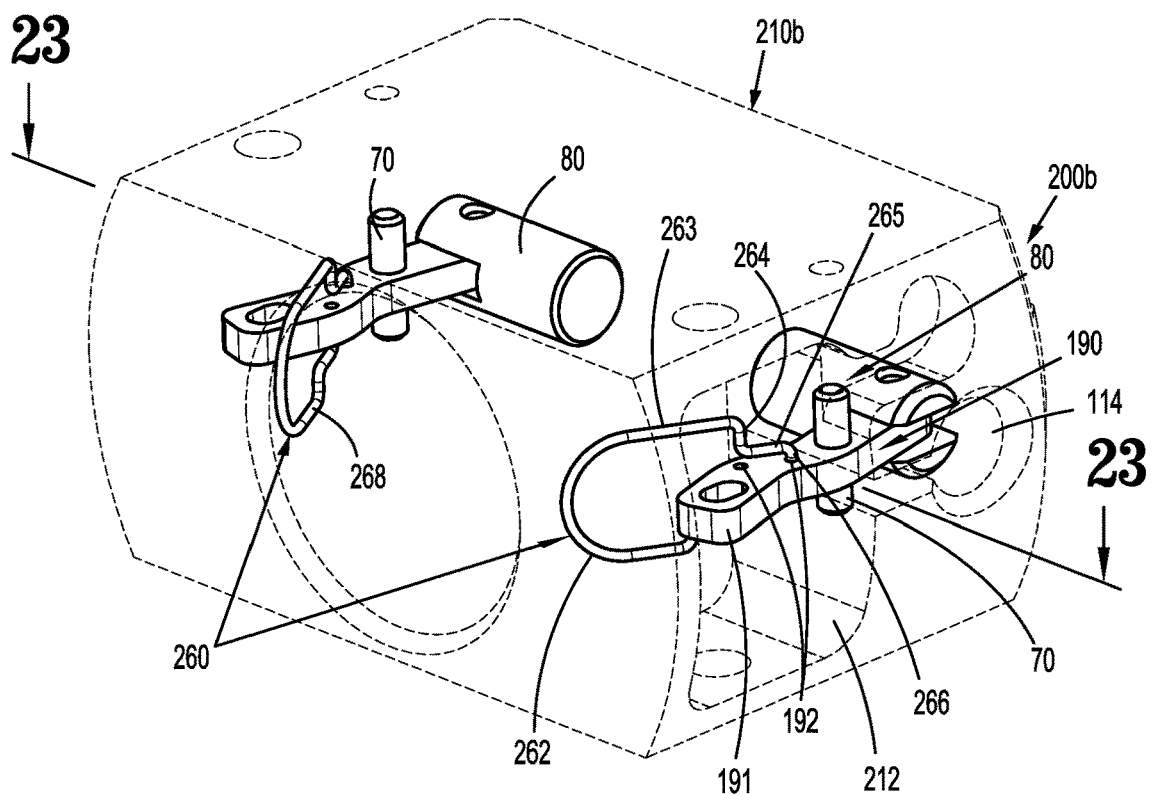
FIG. 22 is a perspective view of the third embodiment of the trocar release assembly with 2-axis springs.
Figure 23:
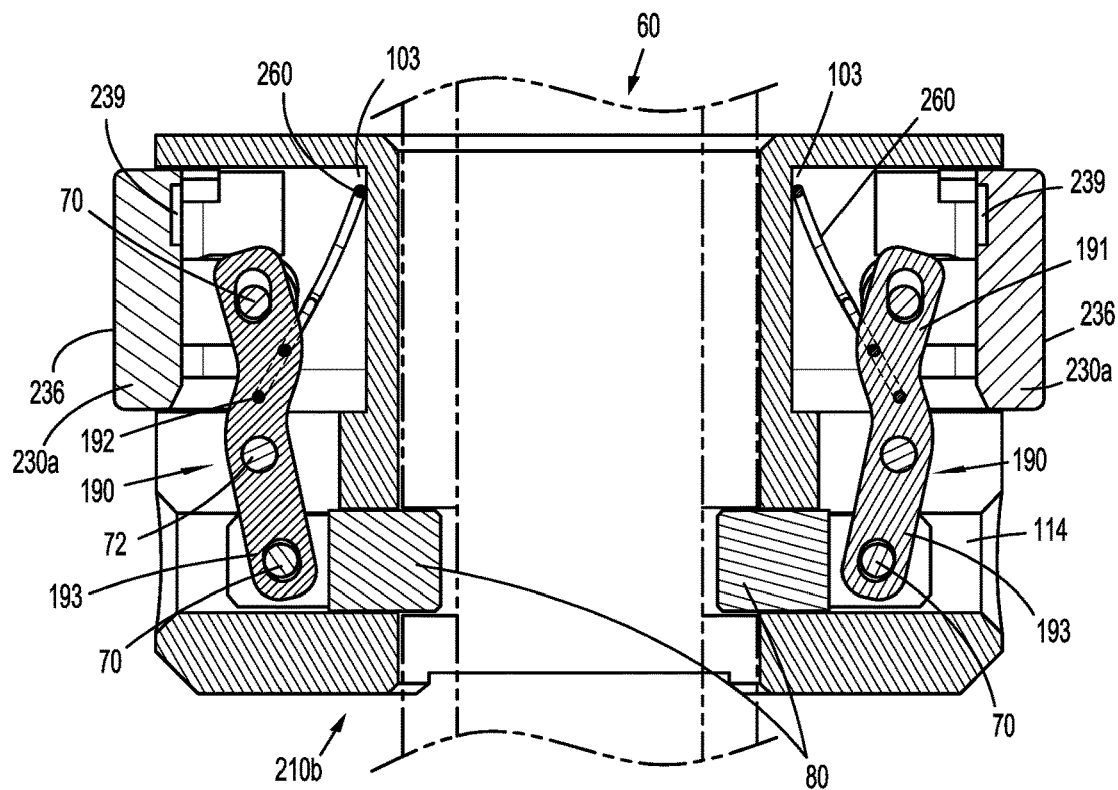
FIG. 23 is a cross-sectional view of the trocar release assembly taken along section line 23-23 of FIG. 22 in a locked configuration.
Figure 24:
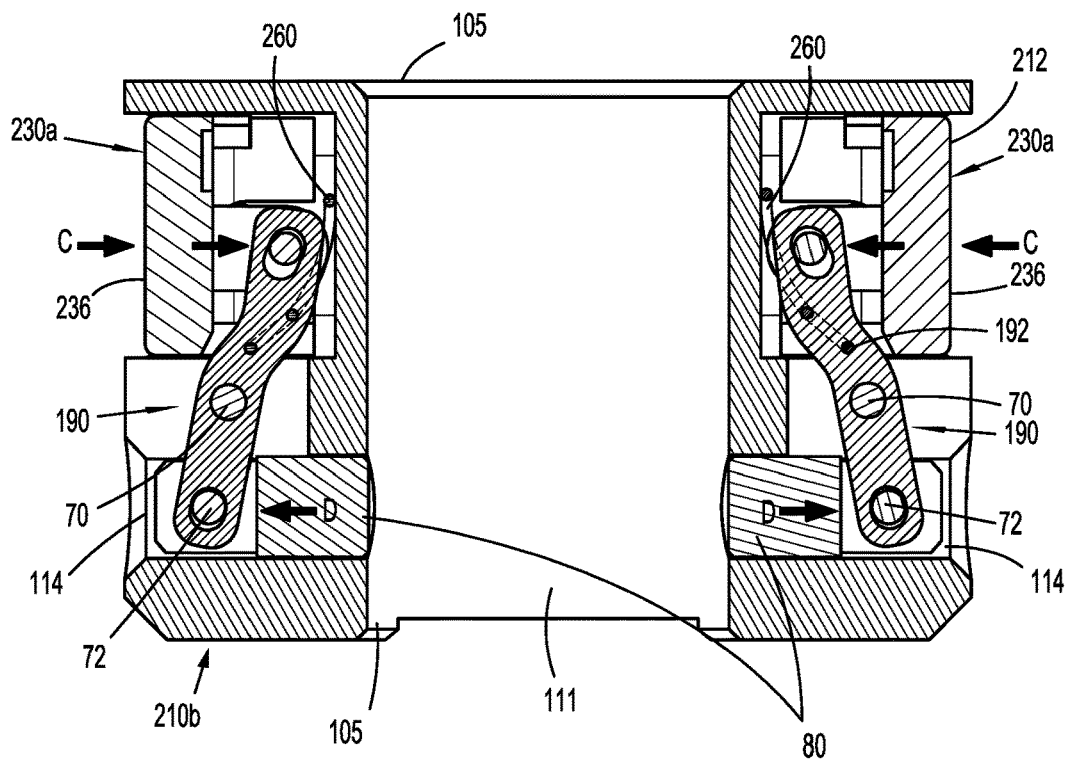
FIG. 24 is a cross-sectional view of the trocar release assembly of FIG. 23 in an unlocked configuration.
Figure 27:
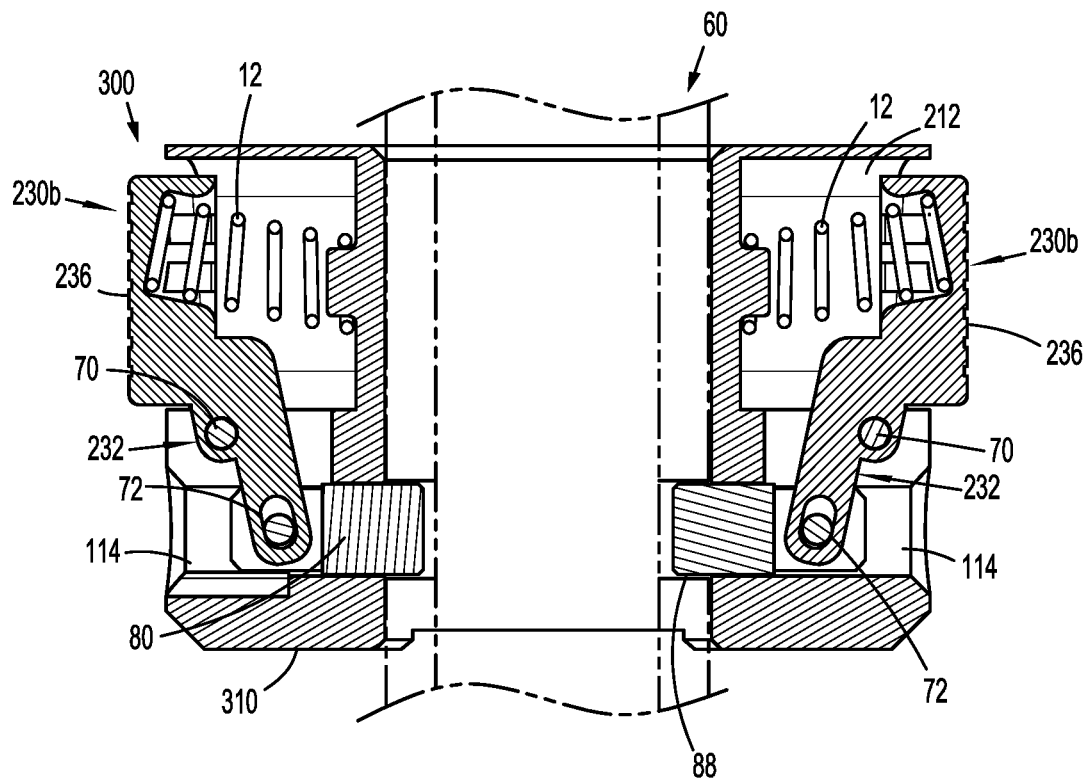
FIG. 27 is a cross-sectional view of the trocar release assembly taken along section line 27-27 of FIG. 25 in a locked configuration.
Figure 28:
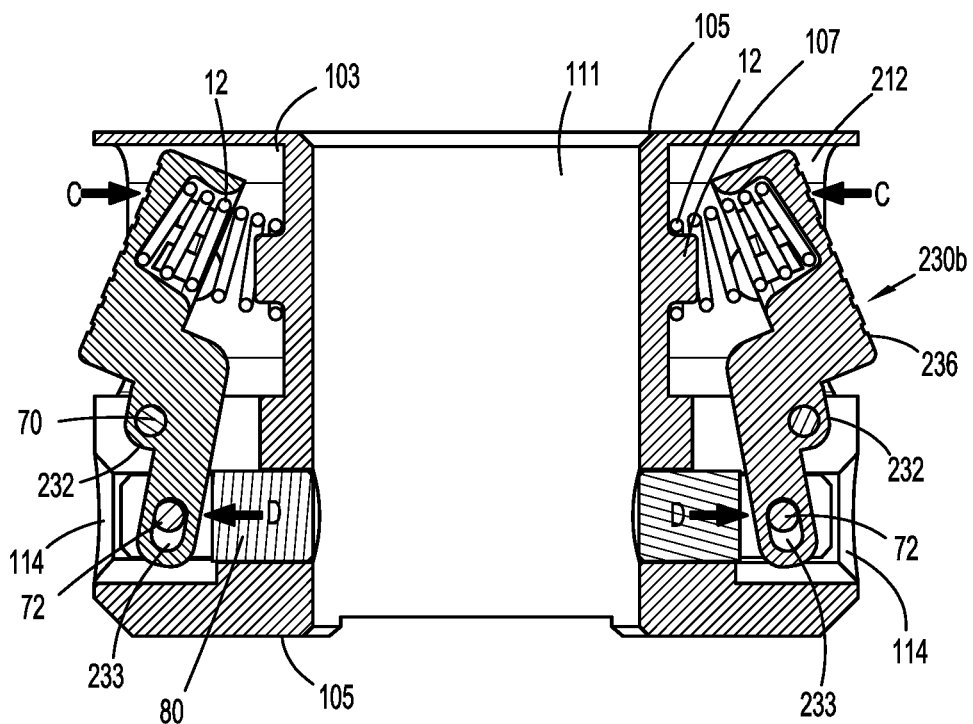
FIG. 28 is a cross-sectional view of the trocar release assembly of FIG. 27 in an unlocked configuration.
Figure 29:
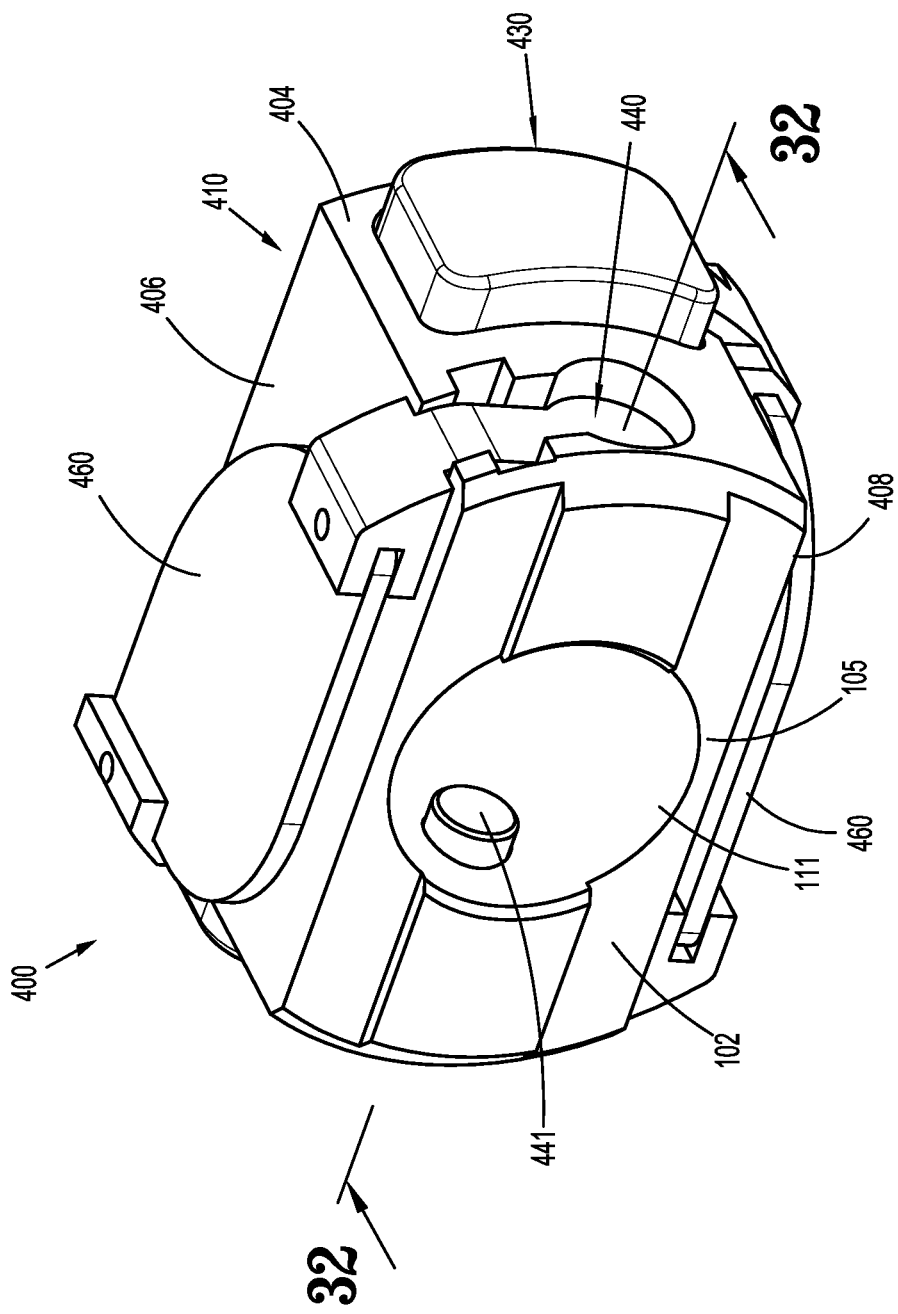
FIG. 29 is a perspective view of a fifth embodiment of a trocar release assembly.
Figure 32:
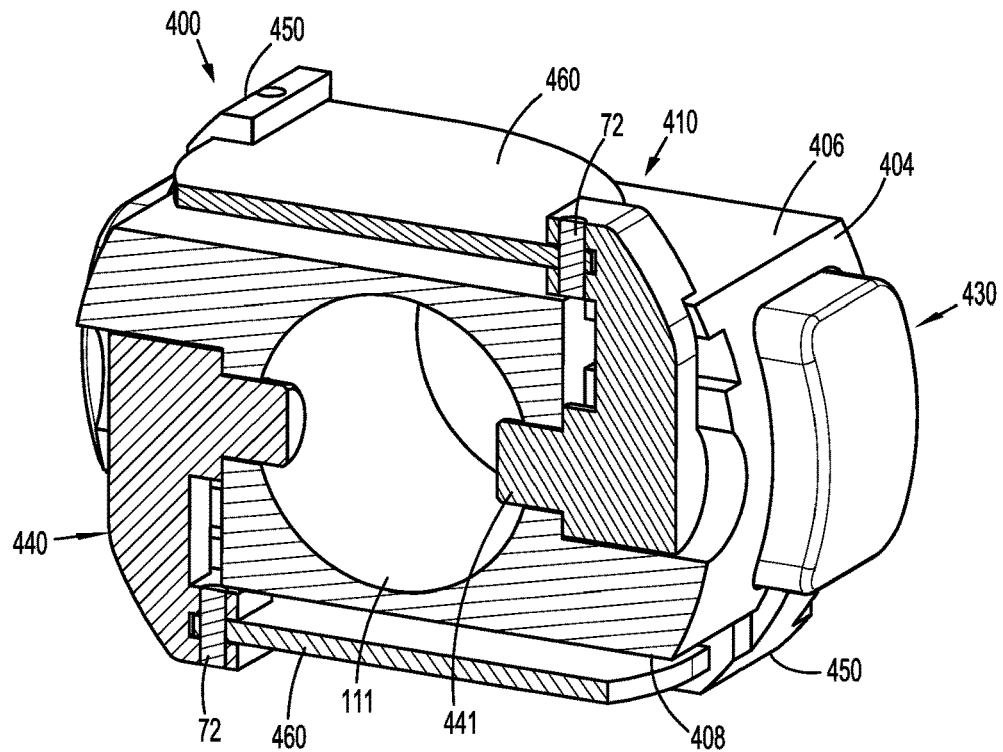
FIG. 32 is a cross-sectional view of the trocar release assembly taken along section line 32-32 of FIG. 29 in a locked configuration.
Figure 33:
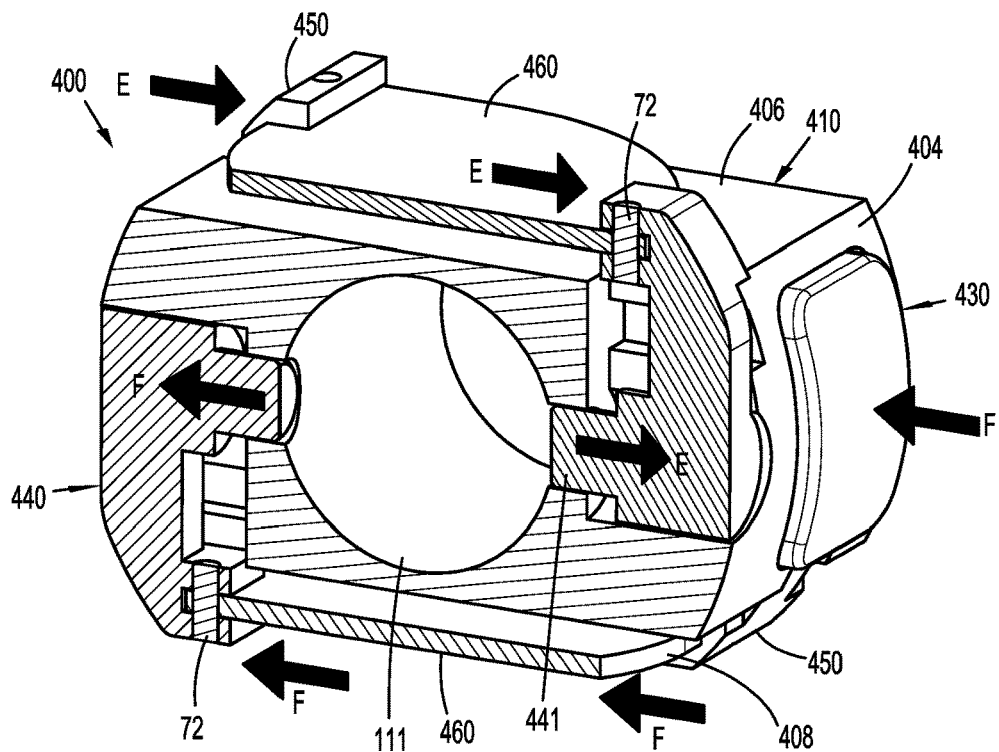
FIG. 33 is a cross-sectional view of the trocar release assembly of FIG. 32 in an unlocked configuration.

Turning now to FIGS. 22-24, another modification of the trocar release assembly is illustrated and generally identified as trocar release assembly 200b. In this variation, the biasing force is supplied by a 2-axis spring 260 instead of the coil spring 12 or leaf spring 254. The 2-axis spring 260 has an arcuate section 262 having legs 268 extending therefrom. Each leg 268 has first, second, and third portions 263, 264, 265. The first and third portions 263, 265 are parallel to one another and interconnected by the second portion 264 that is orthogonal to the first and third portions 263, 265. Prongs 266 extend from the third portions 265 of each leg 268. The first portions 263 of the legs 268 have different lengths such that the prongs 266 are laterally offset from one another thereby defining the two different axes of the 2-axis spring 260. The prongs 266 are received in holes 192 in first section 191 of rocker arm 190. The holes 192 in the first section 191 of the rocker arm 190 are laterally offset from one another. The arcuate section 262 abuts the wall 103 of the recess 212 and applies a biasing force to the first section 191 of the rocker arm 190 and to the release button 230a that is coupled to the first section 191 of the rocker arm 190 as described hereinabove with regards to FIG. 16. The 2-axis spring 260 biases the release button 230a towards the extended position (i.e., outboard) such that the first section 191 of the rocker arm 190 pivots away from the wall 103 of the recess 212 and second section 193 of the rocker arm 190 pivots towards the passage 111 of the housing 210b (i.e., inboard) thereby sliding the retention pin 80 towards the extended position and defining the locked configuration of the trocar release assembly 200b. Depressing the release button 230a in the direction of arrow "C" overcomes the bias of the 2-axis spring 260 and pivots the rocker arm 190 such that the first section 191 is closer to the wall 103 of the recess 212 (i.e., inboard) and the second section 193 moves away from the passage 111 of the housing 210b (i.e., outboard) in the direction of arrow "D", which retracts the retention pin 80 out of the passage 111 thereby defining the unlocked configuration of the trocar release assembly 200b.

Referring now to FIGS. 25-28, a further embodiment of a trocar release assembly is depicted and identified as trocar release assembly 300. Similar to the previous embodiments, the trocar release assembly 300 includes a housing 310 with opposed planar end faces 102, opposed planar top and bottom faces 306, 108, and arcuate side faces 204. Passage 111 extends through the housing 310 between openings 105 in the opposed end faces 102. The passage 111 further includes bores 119 for slidably receiving distal portions 88 of retention pins 80. Each side face 204 includes a recess 212 for slidably receiving a release button 230b therein, a chamber 114 for slidably receiving the retention pin 80, and a slot 219 extending between the chamber 114 and the recess 212. The slot 219 includes opposed openings 216 for receiving pivot pin 70 that pivotably couples an arm 232 of the release button 230b with the retention pin 80. A first end of the arm 232 is secured to the release button 230b and extends therefrom. The arm 232 includes a center opening 231 for receiving the pivot pin 70 such that the arm 232 is pivotable about the pivot pin 70. A second end of the arm 232 includes an oblong hole 233 and is disposed between fingers 82 of the retention pin 80 such that the hole 233 of the second end of the arm 232 is aligned with opposed openings 84 of the fingers 82 such that pin 72 is insertable into the hole 233 and openings 84 to couple the retention pin 80 to the arm 232. A spring 12 (i.e., coil spring) extends between the wall 103 of the recess 212 and an inner surface 238b of the release button 230b. One end of the coil spring 12 is positioned over a stud 107 on the wall 103 of the recess 212 and the other end of the coil spring 12 is positioned in a cut-out 239b of the inner surface 238b of the release button 230b. In this configuration, the coil spring 12 biases the release button 230b towards the extended position (i.e., outboard) such that the first end of the arm 232 pivots away from the wall 103 of the recess 212 and the second end of the arm 232 pivots towards the passage 111 of the housing 310 (i.e., inboard) thereby sliding the retention pin 80 towards the extended position and defining the locked configuration of the trocar release assembly 300. As in the previous embodiment, depressing the release button 230b in the direction of arrow "C" overcomes the bias of the coil spring 12 and pivots the first end of the arm 232 such that the first end is closer to the wall 103 of the recess (i.e., inboard) and the second end moves away from the passage 111 of the housing 310 (i.e., outboard) in the direction of arrow "D", which retracts the retention pin 80 out of the passage 111 thereby defining the unlocked configuration of the trocar release assembly 300.

With reference now to FIGS. 29-33, a further embodiment of a trocar release assembly is illustrated and identified as trocar release assembly 400. Trocar release assembly 400 includes a housing 410 having opposed planar end faces 102 with openings 105 that define a passage 111 therethrough, top and bottom planar faces 406, 408, and arcuate side faces 404. The top and bottom faces 406, 3408 include cut-outs 407 that extend into the side faces 404. The side faces 404 include recesses 412 for slidably receiving release buttons 430 therein and chambers 414 for slidably receiving retention arms 440 therein. In particular, each chamber 414 has a generally key hole configuration with a circular portion 413 that receives a cylindrical retention pin 444 of the retention arm 440 and a slot portion 415 for slidably receiving a post 445 extending from the retention pin 444. The slot portion 415 terminates at the cut-out 407 of the top or bottom face 406, 408 such that a coupler 446 attached to the post 445 is slidable along the top or bottom face 406, 408 of the housing 410 while the post 445 moves through the slot portion 415. As in the previous embodiments, the passage 111 includes bores 119 for receiving distal portions 441 of the retention pins 444. Each retention pin 444 includes a distal portion 441 and a body 442 having a diameter greater than that of the distal portion 441. The coupler 446 has a notch 447 therein and opposed orifices 448 for receiving pins 72. The recess 412 includes a wall (not shown) that is substantially identical to wall 103 of recess 212 (FIG. 23) and slidably receives the release button 430. A spring 12 (i.e., coil spring) is positioned between the wall of the recess 412 and a cavity 436 of an inner surface 438 of the release button 430 for biasing the release button 430 away from the wall of the recess 412 (i.e., outboard). Each release button 430 includes an extension 450 having a notch 452 and opposed orifices 454 for receiving pin 72. A plate 460 is positioned on each of the top and bottom faces 406, 408 for coupling release buttons 430 with retention arms 440. As coupled, the release button 430, the plate 460, and the retention arm 440 define a release assembly attachable to the housing. The top face 406 will be described and it is understood that the bottom face 408 functions in the same fashion. The plate 460 has bores 462 on opposite ends where one end is received in the notch 432 of the release button 430 and the other end is received in the notch 447 of the retention arm 440. As the orifices 448 of the notches 447 and the bores 462 of the plate 460 are aligned, the pins 72 are inserted through the orifices 448 and the bores 462 to couple the plate 460 to one release button 430 and one retention arm 440. As the release button 430 is biased outwards by the spring 12, the retention arm 440 is positioned towards the passage 111 such that the distal portion 441 of the retention pin 444 enters the passage 111 (i.e., extended position) and defines a locked configuration of the trocar release assembly 400. Depressing the release button 430 to overcome the bias of the spring 12 moves the release button 430 towards the passage 111 (i.e., inboard) and slides the plate 460 in the same direction. As the retention arm 440 on the opposite side of the housing 410 is coupled to the release button 430 via the plate 460, the retention arm 440 on the opposite side moves away from the passage 111 of the housing 410 (i.e., outboard) and retracts the distal portion 441 of the retention pin 444 from the bore 119 of the passage 111 (i.e., retracted position) and defining the unlocked configuration of the trocar release assembly 400.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. A trocar release assembly for a surgical stapler comprising:
    a housing having opposed openings defining a passage therethrough, the passage configured to receive a sleeve of a trocar assembly therein;
    a release button movably coupled to the housing, the release button movable between an extended position and a compressed position;
    a first spring disposed between the housing and the release button, the first spring biasing the release button towards the extended position;
    a pin slidably disposed in a chamber of the housing, the pin slidable between an extended position and a retracted position; and
    a second spring operatively coupled with the pin, the second spring biasing the pin towards the extended position.

2. The trocar release assembly of claim 1, wherein moving the release button towards the compressed position slides the pin towards the extended position.

3. The trocar release assembly of claim 1, wherein the compressed position of the release button and the retracted position of the pin define an unlocked configuration of the trocar release assembly.

4. The trocar release assembly of claim 3, further including a sphere disposed between a prong of the release button and a ramp of the pin, the sphere operatively coupling the release button and the pin.

5. The trocar release assembly of claim 4, wherein movement of the release button towards the compressed position propels the sphere along the ramp such that the pin slides towards the retracted position.

6. The trocar release assembly of claim 3, wherein a sleeve of a trocar assembly is insertable into the passage of the housing with the trocar release assembly in the unlocked configuration.

7. The trocar release assembly of claim 1, wherein a distal portion of the pin is engageable with a slot in an outer surface of a sleeve of a trocar assembly to maintain a fixed axial relationship between the trocar release assembly and a trocar assembly.

8. The trocar release assembly of claim 1, further including a plunger having a sloped portion and a third spring, the plunger and the third spring disposed between a prong of the release button and the pin, the third spring biasing the plunger towards the prong of the release button.

9. The trocar release assembly of claim 8, wherein movement of the release button towards the compressed position pushes the sloped portion of the plunger into engagement with an arm of the pin such that the pin slides towards the retracted position.

10. A trocar release assembly for a surgical stapler comprising:
    a housing having opposed openings defining a passage therethrough, the passage configured to receive a sleeve of a trocar assembly therein;
    a release button movably coupled to the housing, the release button movable between an extended position and a compressed position;
    a spring disposed between the housing and the release button, the spring biasing the release button towards the extended position;
    a pin slidably disposed in a chamber of the housing, the pin slidable between an extended position and a retracted position; and
    a rocker arm operably coupling the pin and the release button such that moving the release button towards the compressed position causes the pin to slide towards the retracted position, the rocker arm pivotable about an axle extending through a center of the rocker arm.

11. The trocar release assembly of claim 10, wherein a first end of the rocker arm is pivotably coupled to the pin with a first spindle and a second end of the rocker arm is coupled to the release button.

12. The trocar release assembly of claim 11, wherein movement of the release button towards the compressed position pivots the rocker arm about the axle such that the first end of the rocker arm pivots towards the passage and the second end of the rocker arms pivots away from the passage.

13. The trocar release assembly of 11, wherein the second end of the rocker arm is pivotably coupled to the release button with a second spindle.

14. The trocar release assembly of claim 10, wherein the compressed position of the release button and the retracted position of the pin define an unlocked configuration of the trocar release assembly.

15. The trocar release assembly of claim 14, wherein a sleeve of a trocar assembly is insertable into the passage of the housing with the trocar release assembly in the unlocked configuration.

16. The trocar release assembly of claim 10, wherein a distal portion of the pin is engageable with a slot in an outer surface of a sleeve of a trocar assembly to maintain a fixed axial relationship between the trocar release assembly and a trocar assembly.

17. The trocar release assembly of claim 10, wherein the spring is selected from the group consisting of: a leaf spring, a coil spring, and a two-axis spring.

18. A trocar release assembly for a surgical stapler comprising:
   a tubular shaft;
   a housing having opposed openings defining a passage through the housing, the passage configured to receive a sleeve of a trocar assembly, the housing disposed in the tubular shaft;
   a release button movably coupled to the housing, the release button movable between an extended position and a compressed position;
   a spring disposed between the housing and the release button, the spring spaced from an inner wall of the tubular shaft and biasing the release button towards the extended position;
   a pin slidably disposed in a chamber of the housing, the pin slidable between an extended position and a retracted position; and
   a plate coupling the release button and the pin such that movement of the release button towards the compressed position slides the pin towards the retracted position, the plate slidable relative to the housing.

19. The trocar release assembly of claim 18, wherein the compressed position of the release button and the retracted position of the pin define an unlocked configuration of the trocar release assembly.

20. The trocar release assembly of claim 18, wherein a distal portion of the pin is engageable with a slot in an outer surface of a sleeve of a trocar assembly to maintain a fixed axial relationship between the trocar release assembly and a trocar assembly.

21. The trocar release assembly of claim 20, wherein a sleeve of a trocar assembly is insertable into the passage of the housing with the trocar release assembly in the unlocked configuration.

* * * * *